(12) United States Patent
Omary

(10) Patent No.: US 8,580,397 B2
(45) Date of Patent: Nov. 12, 2013

(54) ORGANIC LIGHT-EMITTING DIODES FROM HOMOLEPTIC SQUARE PLANAR COMPLEXES

(75) Inventor: Mohammad A. Omary, Denton, TX (US)

(73) Assignee: University of North Texas, Denton, TX (US)

( * ) Notice: Subject to any disclaimer, the term of this patent is extended or adjusted under 35 U.S.C. 154(b) by 399 days.

(21) Appl. No.: 13/055,974

(22) PCT Filed: Jul. 8, 2009

(86) PCT No.: PCT/US2009/049938
§ 371 (c)(1),
(2), (4) Date: Apr. 12, 2011

(87) PCT Pub. No.: WO2010/016990
PCT Pub. Date: Feb. 11, 2010

(65) Prior Publication Data
US 2011/0260145 A1    Oct. 27, 2011

Related U.S. Application Data

(60) Provisional application No. 61/188,428, filed on Aug. 8, 2008, provisional application No. 61/176,190, filed on May 7, 2009.

(51) Int. Cl.
*H01L 51/54* (2006.01)
*C09K 11/06* (2006.01)

(52) U.S. Cl.
USPC ........... 428/690; 428/917; 313/504; 313/506; 252/301.16; 257/40; 257/89; 257/102; 257/E51.044; 548/103

(58) Field of Classification Search
None
See application file for complete search history.

(56) References Cited

U.S. PATENT DOCUMENTS

| 7,002,013 B1* | 2/2006 | Chi et al. | 546/10 |
| 2002/0134984 A1* | 9/2002 | Igarashi | 257/79 |
| 2006/0286404 A1* | 12/2006 | Wu | 428/690 |

OTHER PUBLICATIONS

European Patent Office; Response to Office Action; European Application No. 09790155.7; Jan. 5, 2012.
Brooks, J., Synthesis and Characterization of Phosphorescent Cyclometalated Platinum Complexes, Inorganic Chemistry, 2002, 3055-3066, 41, American Chemical Society.
D'Andrade, B. W., Controlling Exciton Diffusion in Multilayer White Phosphorescent Organic Light Emitting Devices, Advanced Materials, 2002,147-151, 14:2.
Ma, B., et al., Platinum Binucleur Complexes as Phosphorescent Dopants for Monochromatic and White Organic Light-Emitting Diodes, Advanced Functional Materials, 2006, 2438-2446, 16.
Misra, A., et al., White organic LEDs and their recent advancements, Semiconductor Science and Technology, 2006, R35-R47, 21, Institute of Physics Publishing.

(Continued)

*Primary Examiner* — Michael H Wilson
(74) *Attorney, Agent, or Firm* — Jackson Walker L.L.P.

(57) ABSTRACT

Homoleptic square planar complexes [M(NΛN)$_2$], wherein two identical NΛN bidentate anionic ligands are coordinated to the M(II) metal center, including bidentate square planar complexes of triazolates, possess optical and electrical properties that make them useful for a wide variety of optical and electrical devices and applications. In particular, the complexes are useful for obtaining white or monochromatic organic light-emitting diodes ("OLEDs"). Improved white organic light emitting diode ("WOLED") designs have improved efficacy and/or color stability at high brightness in single- or two-emitter white or monochrome OLEDs that utilize homoleptic square planar complexes, including bis[3,5-bis(2-pyridyl)-1,2,4-triazolato]platinum(II) ("Pt(ptp)$_2$").

38 Claims, 16 Drawing Sheets

(56) References Cited

OTHER PUBLICATIONS

Newman, C. R., et al., Introduction to Organic Thin Film Transistors and Design of n-Channel Organic Semiconductors, Chem. Mater. 2004, 4436-4451, 16, American Chemical Society.

Qi, X. et al., Stacked White Organic Light Emitting Devices Consisting of Seperate Red, Green and Blue Elements, Applied Physics Letters, 2008, 193306-1 to 193306-3, 93. American Institute of Physics.

Ramos-Ortiz, G., et al, Forster Energy Transfer from a Flourescent Dye to a Phosphorescent Dopant: a concentration and Intensity Study, Phys. Chem. Chem. Phys., 2002, 4109-4114, 4, The Owner Societies 2002.

Sun, Y., et al., Management of Single and Triplet Excitons for Efficient White Organic-Light-Emitting Devices, Nature, 2006, 908-912, 440:13, Nature Publishing Group.

Wu, Y.Z., Highly Efficient Pure Blue Electroluminescence from 1,4-bis[2-3N-ethylcarbazoryl)vinyl]benzene, Applied Physics Letters, 2003, 5077-5079, 83:24, American Institute of Physics.

Yang, X., et al., Efficient Blue- and White-Emitting Electrophosphorescent Devices Bases on Platinum (II) [1,3-Difluoro-4, 6-di(2-pyridinyl)benzene] Chloride, Advanced Materials, 2008, 2405-2409, 20.

Yang, X., et al., Highly Efficient Excimer-based White Phosphorescent Devices with Improved Power Efficiency and Color Rendering Index, Applied Physics Letters, 2008, 193305-1 to 193305-3, 93.

D'Andrade, B. W., et al,. Efficient Organic Electrophosphorescent White-Light-Emitting Device with a Triple Doped Emissive Layer, Advanced Materials, 2004, 624-628, 16:7.

Williams, E. L., et al., Excimer-Based White Phosphorescent Organic Light Emitting Diodes with Nearly 100% Internal Quantum Efficiency, Advanced Materials, 2007, 197-202, 19.

Kanno, H., et al., Stacked White Organic Light-emitting Devices Bases on a Combination of Fluorescent and Phosphorescent Emitters, Applied Physics Letters, 2006, 023503-1 to 023503-3, 89, American Institute of Physics.

European Patent Office; Office Action; European Application No. 09790155.7; Sep. 12, 2011.

\* cited by examiner

M = Pt, Pd, or Ni
R = pyridyl, CF₃, F, Cl, Br, COOR', NO₂, CN, H, n-alkyl, *etc.*

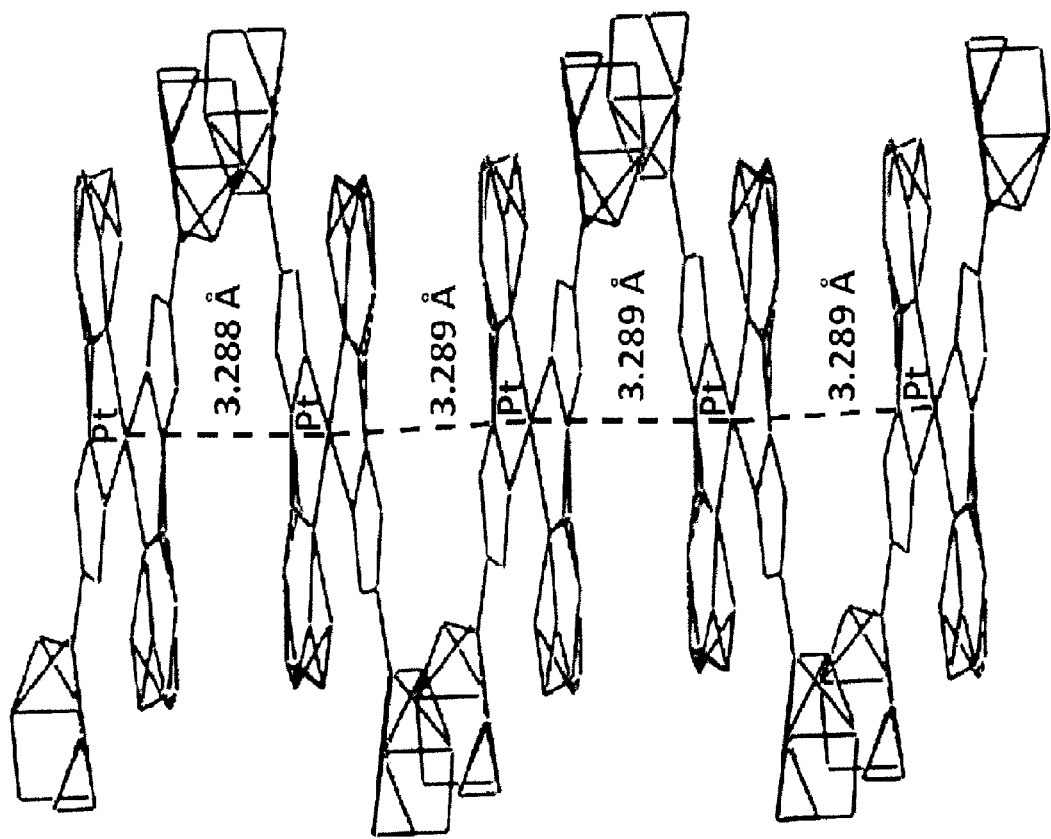

ORGANIC LIGHT-EMITTING DIODES FROM HOMOLEPTIC SQUARE PLANAR COMPLEXES

This application claims priority to U.S. Provisional Patent Application Ser. No. 61/188,428, entitled "Bidentate Square Planar Complexes of Triazolates and Uses Thereof," filed Aug. 8, 2008, and U.S. Provisional Patent Application Ser. No. 61/176,190, entitled "Improved Organic Light-Emitting Diodes From Homoleptic Square Planar Complexes," filed May 7, 2009, the entire contents of which are hereby incorporated by reference.

The present invention used in part funds from the Department of Energy, DOE, Cooperative Agreement No. DE-FC26-06NT42859. The United States Government may have certain rights in the invention.

BACKGROUND

This invention pertains to bidentate square planar complexes of triazolates and particularly to their uses in organic light emitting diodes ("OLEDs"), n-type semiconductor materials, and other applications. This invention also pertains to improved efficacy and/or color stability at high brightness in single- or two-emitter white or monochrome OLEDs that utilize homoleptic square planar complexes of the general type [M(N^N)$_2$], wherein two identical N^N bidentate anionic ligands are coordinated to the M(II) metal center, as exemplified by the preferred embodiment bis[3,5-bis(2-pyridyl)-1,2,4-triazolato]platinum(II) ("Pt(ptp)$_2$").

Luminescent organic or metal-organic molecular materials have a range of applications. These include organic light emitting diodes ("OLEDs") that exhibit white or monochrome electroluminescence. Such devices may be utilized in solid-state lighting ("SSL"), which can greatly decrease the energy demand of current lighting technologies that account for 22% of total electrical power consumption in the U.S., and also for video display in electronic devices such as TV, camcorders, monitors, cell phones, etc. In particular, utilization of phosphorescent metal-organic complexes in OLEDs has allowed higher device performance than that allowed by fluorescent organic materials because the phosphorescent metal-organic complexes allow radiative recombination of both triplet and singlet excitons (with an upper limit of 100% efficiency compared to 25% for fluorescent organic materials).

OLEDs have emerged as promising candidates for solid-state lighting and display applications. For monochromatic electroluminescent devices, 100% internal quantum efficiency has been reported using phosphorescent molecules that harvest both singlet and triplet excitons, representing a four-fold increase in efficiency compared to electrofluorescent devices. White OLEDs ("WOLEDs") can now exceed the ~12-17 µm/W power efficiency of conventional incandescent lamps. Efficient WOLED strategies include red, green, and blue phosphorescent dopants in a single emissive layer (D'Andrade, 2004), phosphor-doped host layers in a stacked configuration (Qi, 2008), and a stacked combination of fluorescent and phosphorescent dopants (Kanno, 2006). The most common approach for creating WOLEDs is typically the combination of multiple emitters, for example red, green, and blue, or RGB emitters. This approach usually requires sophisticated device structures and results in difficult-to-control processing conditions, differential aging of RGB emitters, and/or energy transfer to the red color center (Misra, 2006; D'Andrade, 2004). The first instance whereby a single dopant was used to produce white electrophosphorescence in an OLED with standard device structures and materials (D'Andrade, 2002) produced performance metrics that do not meet today's standards for SSL in power efficiency and device stability (D'Andrade, 2004). To replace conventional incandescent or fluorescent light sources, WOLEDs must exhibit high color rendering index ("CRI"), stability at a high luminance of ≥1000 cd/m$^2$, and long operational lifetimes exceeding 10,000 hours.

Recently, higher external quantum efficiency and power efficiency were demonstrated in fluorescent/phosphorescent WOLEDs employing a blue fluorophore combined with green and red phosphors in a common host (Sun, 2006). The improvement in performance is attributed to judicious harvesting of singlet and triplet excitons. Resonant energy transfer from the host to dopants eliminates exchange energy loss, resulting in improved efficiencies.

Self-quenching and long radiative lifetimes in phosphorescent emitters are partly responsible for decreased efficiency and stability in OLEDs (Baldo, 1998; D'Andrade, 2004). Thus, new materials and device concepts that overcome these issues are critically needed for OLEDs with improved efficacy and/or color stability at high brightness.

SUMMARY

The present invention relates generally to a class of metal-organic complexes that possess optical and electrical properties which make them useful for a variety of optical and electronic devices and applications. These include homoleptic square planar complexes of the general type [M(N^N)$_2$], wherein two identical N^N bidentate anionic ligands are coordinated to the M(II) metal center. The materials include square planar complexes of triazolate ligands with a variety of substituents and metal ions such as Pt(II), Pd(II), and Ni(II). This invention also pertains to organic light emitting diodes ("OLEDs"), and more particularly to white OLEDs ("WOLEDs"). This invention also pertains to organic thin film transistors ("OTFTs"), and more particularly to n-type OTFTs, as well as semiconducting metal-organic materials. The present invention also relates generally to improved efficacy and/or color stability at high brightness in single- or two-emitter monochrome or white OLEDs.

Use of the bidentate square planar complexes of triazolate ligands allows control of chromaticity to achieve white OLED devices, in which their electroluminescence ("EL") emission profile and color coordinates do not shift significantly with voltage, and they maintain high power and luminance efficiencies to remain near the peak values even at high brightness, voltage, and/or current density. The complexes also allow excellent control of the chromaticity to achieve not only white devices but also monochrome devices, including the highly-coveted blue OLEDs. Electrophosphorescent OLEDs with high efficiency, stability, and genuine blue chromaticity are difficult to achieve while the materials in this invention are useful for such devices. The complexes can be varied with a variety of metal ions as well as substituent ligands, with a preferred form utilizing platinum and the ligand ptp (3,5-bis(2-pyridyl)-1,2,4-triazolate).

The metal-organic complexes can also be useful as n-type molecular materials for use in thin-film transistors ("TFTs") and organic semiconductors. This occurs due to crystal polymorphs in which extended linear chains of overlapping stacked complexes lead to the semiconducting behavior.

One improved WOLED design, which can be characterized as providing "cool white" light, uses a simplified fluorescent/phosphorescent dopant model with only one broadband yellow phosphor instead of two different green and red phosphors. The stacked architecture uses a phosphorescent emissive layer sandwiched between two doped fluorescent layers separated by thin spacer layers of undoped host. As an example, the cool WOLED can include N,N'-diphenyl-N,N'-bis(1-naphthyl)-1,1'-biphenyl-4,4''-diamine ("NPB") as a hole transporting layer, 1,3,5-tris(phenyl-2-benzimidazolyl)-benzene ("TPBI") as an electron transporting layer, 4,4'-bis(carbazol-9-yl)biphenyl ("CBP") as host and spacer, and 4,4'-bis(9-ethyl-3-carbazovinylene)-1,1'-biphenyl ("BCzVBi") deep-blue fluorescent and bis[3,5-bis(2-pyridyl)-1,2,4-triazolato]platinum(II) ("Pt(ptp)$_2$") yellow phosphorescent dopants.

Another improved WOLED design, which can be characterized as providing "warm white" light, uses only one phosphor in one or two different emission regions, one providing shorter wavelengths in the blue-green region and the other providing longer wavelengths in the yellow-orange-red region. As an example, the warm WOLED can include N,N'-diphenyl-N,N'-bis(1-naphthyl)-1,1'-biphenyl-4,4''-diamine ("NPB") as a hole transporting layer, N,N'-dicarbazolyl-3,5-benzene (mCP) as an electron- and exciton-blocking layer, 1,3,5-tris(phenyl-2-benzimidazolyl)-benzene ("TPBI") as an electron transporting layer, 4,4'-bis(carbazol-9-yl)biphenyl ("CBP") as host for one emissive layer doped with 1-10% of the Pt(ptp)$_2$ phosphorescent dopant, and another emissive layer consisting of a neat or highly-doped (>30%) film of Pt(ptp)$_2$.

To produce the improved cool WOLED, as an example, there is first a systematic introduction of deep-blue fluorescence from a deep-blue fluorescent dopant such as 4,4'-(bis (9-ethyl-3-carbazovinylene)-1,1'-biphenyl to broad-band yellow phosphorescence from a broad-band yellow phosphorescent dopant such as bis[3,5-bis(2-pyridyl)-1,2,4-triazolato]platinum(II) in a common host, such as 4,4'-bis(carbazol-9-yl)biphenyl ("CBP"). The improved cool WOLED exhibits striking stability of color and efficiency, as manifest by parameters at high brightness of 1000 cd/m$^2$ sustaining 94-122% their values at 50 cd/m$^2$.

To produce the improved warm WOLED, as an example, there is first a systematic introduction of blue-green phosphorescence from a lightly-doped (1-10% by volume) layer of the Pt(ptp)$_2$ phosphorescent dopant in a host such as CBP to broad-band yellow-orange-red phosphorescence from a neat or highly-doped (>30%) layer of the same Pt(ptp)$_2$ phosphor. The improved warm WOLED exhibits excellent color rendering index (CRI) values as high as 82 and striking stability of color and efficiency with very little roll-off at high brightness of 1000 cd/m$^2$.

Another example for an improved warm WOLED design involves using only one neat or highly-doped film of Pt(ptp)$_2$. Altering the thickness of the emissive layer, the host material in the highly-doped type of WOLED, the material or the thickness of other layers besides the emissive layer can lead to improvements in the device performance and white color metrics characterized as CIE coordinates or color rendering index (CRI).

Efficiency improvement in monochrome and white OLEDs that utilize bidentate square planar complexes of triazolates such as Pt(ptp)$_2$ are achieved by further variation of device structure. As an example, adding a thin layer of mCP as an electron- and exciton-blocking layer after the hole transporting layer NPB or replacing both by 1,1-bis-(4-bis(4-methyl-phenyl)-amino-phenyl)-cyclohexane ("TPAC") results in a dramatic improvement of OLEDs that include neat or doped emissive layers of Pt(ptp)$_2$. Significant improvement can be further achieved by using a different material in the electron transporting layer, such as other electron-transporting materials such as tris(2,4,6-trimethyl-3-(pyridin-3-yl) phenyl)borane ("3TPYMB" or "TPYMB"), 1,3,5-tris(m-pyrid-3-yl-phenyl)benzene ("TmPyPB"), 1,3,5-tris(p-pyrid-3-yl-phenyl)benzene ("TpPyPB"), 4,7-diphenyl-1,10-phenanthroline ("BPhen"), or other suitable materials.

DETAILED DESCRIPTION OF PREFERRED EMBODIMENTS

Generally, the present invention relates to homoleptic square planar complexes of the general type [M(N^N)$_2$], wherein two identical N^N bidentate anionic ligands are coordinated to the M(II) metal center. Examples include bidentate square complexes of triazolates, as well as organic light emitting diodes ("OLEDs") fabricated according to an improved process and having improved color stability and efficiency.

Homoleptic square planar complexes of the general type [M(N^N)$_2$] have two identical N^N bidentate anionic ligands coordinated to the M(II) metal center. Specific examples include bidentate square planar complexes of triazolates. Variants of this structure include other N-donor bidentate ligands such as those containing a pyrazolate instead of a triazolate group, or an imidazole group instead of a pyridine group.

OLEDs with high brightness and efficiency parameters, tunable color coordinates including a white color, and electrical behavior suggestive of an n-type semiconductor can be obtained using bidentate square complexes of (pyridyl)triazolates, such as the complex $Pt(ptp)_2$, where ptp=3,5-bis(2-pyridyl)-1,2,4-triazolate. The complexes demonstrate remarkable photoluminescence ("PL") behavior, particularly for $Pt(ptp)_2$, including monomer, excimer, and extended excimer phosphorescence for solids of the pure compound as well as combinations of these emissions to achieve white and monochrome colors either in solution or in doped thin films of varying concentration of $Pt(ptp)_2$ in the OLED host material CBP. These PL properties guide the design of the OLEDs, which attain electroluminescence ("EL") properties that mirror the PL changes. In addition, two structures exist for the complex $Pt(ptp)_2$, one that has pairs of molecules stacking in a manner that stabilizes excimer formation while the other has molecules stacked in infinite chains. The latter stacking stabilizes extended excimer emission and also suggests a semiconducting behavior.

Figure 1:
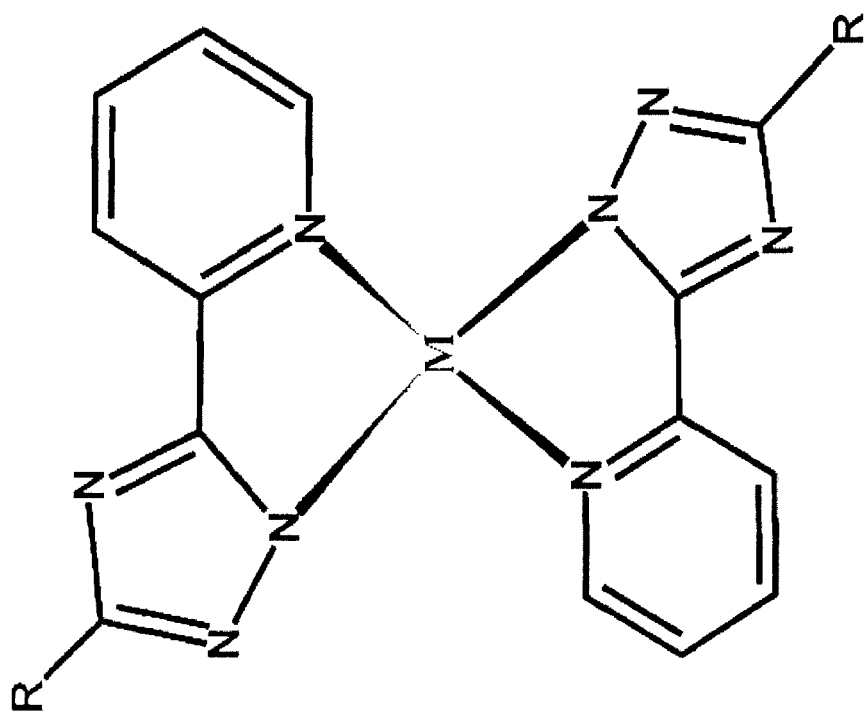
FIG. 1 shows the general chemical structure of some of the bidentate square complexes of triazolates.

The bidentate square complexes of triazolates have the general structure shown in FIG. 1, in which M can be Pt, Pd, or Ni, and in which R can be pyridyl, $CF_3$, F, Cl, Br, COOR', $NO_2$, CN, H, n-alkyl, or other suitable substituents. Bypyridine (bpy) and thiophene can also be used as the R substituent.

With regard to varying the metal ("M") in the complexes as they are shown in FIG. 1, the use of palladium (Pd) favors the formation of n-type OTFTs. Nickel (Ni) is a good choice for the metal because it is cheaper for both OLEDs and OTFTs. Changing the ligand substituent ("R") to H creates better stacking. Using the substituents F, Cl, Br, CN, COOR', or $NO_2$ (n-type) is favorable because these are electron-poor substituents. Better blue color can be obtained with electron-poor substituents to achieve the highly coveted blue electrophosphorescent OLEDs with high efficacy and stability. Solubilizing groups such as n-alkyl are also helpful for solution processing.

Organometallic cyclometalated platinum(II) complexes have been investigated as emissive dopants in WOLEDs (Brooks, et al. 2002), typically by combining the broad-band excimeric emission of the Pt(II) phosphor with either a different Ir(III) blue phosphor or the monomer emission of the same Pt(II) phosphor (D'Andrade, 2002; D'Andrade, 2004; Williams, 2007; Brooks, 2002; Yang, *Adv. Mater.* 2008; Yang, *Appl. Pys. Lett.* 2008; Ma, 2006). The $Pt(ptp)_2$ complex used herein in the improved WOLEDs is non-organometallic/non-cyclometalated (no C—Pt bonds) with (pyridyl)triazolate N,N-coordination of two ptp bidentate ligands to platinum (II). The presence of six aromatic rings per molecule and control of self-association render excellent chromophoric and luminescence properties in the complex, including bright color-tunable photo- and electroluminescence across the visible region by varying the doping level.

The bidentate square complexes can be used to obtain white, near-white, and monochrome OLEDs that utilize the electroluminescence of $Pt(ptp)_2$ and other material variations, such as by using complexes of (pyridyl)triazolates. This includes near-white OLEDs based on EL emission of $Pt(ptp)_2$. This also includes white and near-white OLEDs based on a combination of the EL emissions of $Pt(ptp)_2$ and another emitter in the same device. Monochrome OLEDs (including blue) can also be obtained using the EL emission of $Pt(ptp)_2$. White and near-white OLEDs and monochrome OLEDs (including blue) can also be obtained using EL emission of bidentate square planar platinum(II) complexes of (pyridyl) triazolates, with or without another emitter in the same device. White and near-white OLEDs and monochrome OLEDs (including blue) can also be obtained using EL emission of bidentate square planar nickel(II) complexes of (pyridyl)triazolates, with or without another emitter in the same device. Acceptable ranges of concentration of the complexes within the CBP solid matrix can be determined intuitively as further described in the examples below. Altering the concentration of the complexes allows a shift in the color scheme.

Applications of the bidentate square complexes to obtain semiconducting material are also significant. A central component of any molecular electronic device is the transistor. The largest application of thin-film transistors ("TFTs") today is for active matrix backplanes for flat panel or flexible displays. The primary commercial material for FETs is hydrogenated amorphous silicon (a-Si:H), although other inorganic and organic materials are under intensive investigation for higher mobility, stability, and lower fabrication cost. A major unsolved challenge that remains is inferior performance and/or stability of organic TFTs ("OTFTs"), especially n-type (or "n-channel") devices (Newman, 2004). Circuit styles available with either a-Si:H or pentacene are all ratioed logic, and consume much more power per gate at a given speed than the industry standard CMOS (complementary metal-oxide semiconductor). CMOS is formed using both n-type and p-type TFTs and is the preferred circuit style for digital logic and high performance analog circuitry. The ability to fabricate organic-semiconductor based CMOS circuits would provide a technology to build a flexible CMOS structured ASIC (application-specific integrated circuit), similar to a field programmable gate array. The essential analog circuit needed is an operational amplifier. This will require both n-FET and p-FET devices that have stable threshold voltages and mobilities. Most organic semiconductors are electron-rich (p-type) with the most common examples being pentacene and phthalocyanins such as CuPc. For electronic devices based on organic or molecular materials, both p- and n-type materials are needed.

Materials in this invention belong to the rare class of n-type molecular materials. Flexible electronic devices require organic materials of both p- and n-type, whereas current CMOS technology usually utilizes only p-type organic materials while amorphous silicon is used for the n-type material. Thus, molecular materials such as $Pd(ptp)_2$ and other embodiments have a great potential to be utilized in all-organic CMOS and flexible electronic devices. Crystals of the $Pt(ptp)_2$ complex exhibit two polymorphs with different packing forms: (a) solvated light yellow crystals, and (b) dry orange crystals. While form (a) has the molecules arranged as poorly-overlapping, offset adjacent molecular units and contains a solvent (methanol) molecule that is H-bonded to the complex, form (b) has extended linear chains of strongly overlapping stacked complexes and short Pt—Pt intermolecular distances (3.289 Å).

Applications of the bidentate square complexes of (pyridyl)triazolates include OTFTs, n-type OTFTs, and CMOS devices including an n-type semiconductor. These devices can be obtained using bidentate square planar palladium(II) complexes of (pyridyl)triazolates, bidentate square planar nickel(II) complexes of (pyridyl)triazolates, and bidentate square planar platinum(II) complexes of (pyridyl)triazolates. Square planar complexes of (pyridyl)trizaolates can be used to create conducting and semiconducting solids (thin films, single crystals, or pressed pellets).

In additional embodiments, sensors utilizing square planar complexes of (pyridyl)triazolates can also be created, including sensors for temperature, pressure, metal ions, pH, and other parameters. For example, the uncoordinated pyridine group can act as an "eye" for binding of protons, thus sensing pH, or for binding metal ions, for sensing heavy metals. In additional embodiments, the uncoordinated pyridine group can be used as a ligand to coordinate to other metal ions to make multinuclear complexes or coordination polymers with modified optical properties. Using bipyridine (bpy) or thiophene as the R substituent can assist in binding hard and soft metals, respectively, which allows the creation of a broader range of sensors.

Figure 2:
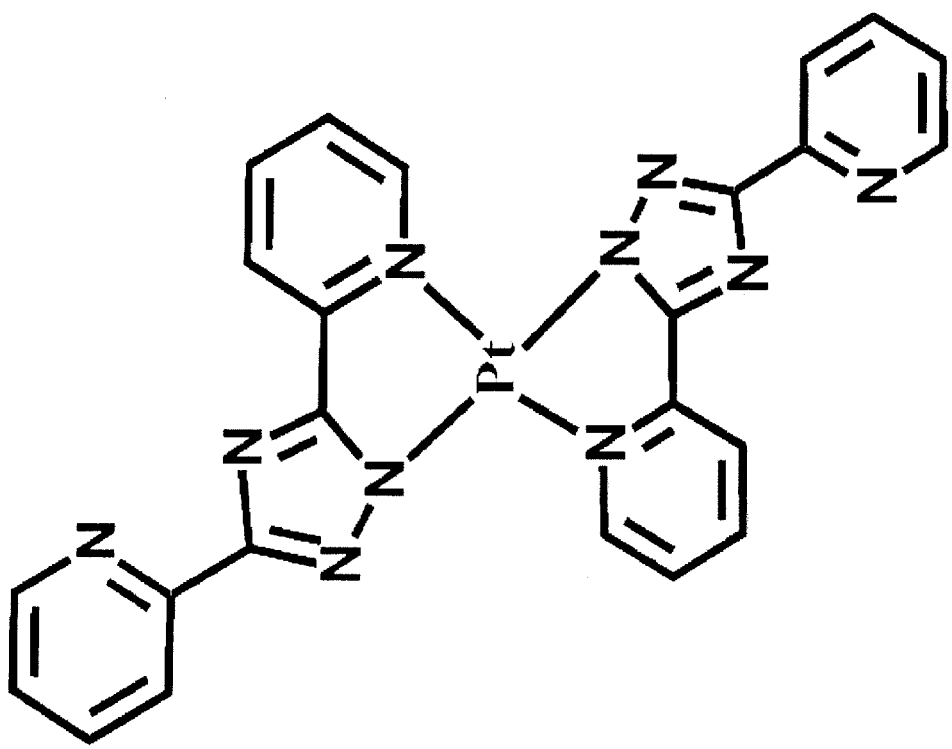
FIG. 2 shows the molecular structure of Pt(ptp)$_2$.

Additional embodiments pertain to OLED designs including single- or two-emitter white or monochrome OLEDs that utilize bidentate square planar complexes of triazolates such as bis[3,5-bis(2-pyridyl)-1,2,4-triazolato]platinum(II) (Pt(ptp)$_2$) to obtain high brightness, improved efficacy, and color stability. The molecular structure of Pt(ptp)$_2$ is shown in FIG. 2.

One improved WOLED design, which can be characterized as providing "warm white" light with a high color rendering index (CRI) close to the ideal 80-100 values, uses only one phosphor that can be in two different emission regions, one providing shorter wavelengths in the blue-green region and the other providing longer wavelengths in the yellow-orange-red region.

One improved WOLED design that is characterized as providing "cool white" light uses a simplified fluorescent/phosphorescent dopant model with only one broad-band yellow phosphor instead of two different green and red phosphors. The stacked architecture uses a phosphorescent emissive layer sandwiched between two doped fluorescent layers separated by thin spacer layers of undoped host. Examples of suitable host materials include 4,4'-bis(carbazol-9-yl)biphenyl ("CBP"), 4,4'-Bis(9-carbazolyl)-2,2'-Dimethyl-biphenyl ("CDBP"), N,N'-dicarbazolyl-3,5-benzene ("mCP"), and 4,4',4"-tris(N-carbazolyl)triphenylamine ("TCTA").

An example of the warm WOLED can include N,N'-diphenyl-N,N'-bis(1-naphthyl)-1,1'-biphenyl-4,4"-diamine ("NPB") as a hole transporting layer, N,N-dicarbazolyl-3,5-benzene ("mCP") as an electron- and exciton-blocking layer, 1,3,5-tris(phenyl-2-benzimidazolyl)-benzene ("TPBI") as an electron transporting layer, 4,4'-bis(carbazol-9-yl)biphenyl ("CBP") as host for one emissive layer doped with 1-10% of the Pt(ptp)$_2$ phosphorescent dopant, and another emissive layer consisting of a neat or highly-doped (>30%) film of Pt(ptp)$_2$.

Doping concentrations by volume of dopant to host material of approximately 30% or greater for the Pt(ptp)$_2$ phosphor and approximately 5% for a deep-blue fluorophore such as 4,4'-(bis(9-ethyl-3-carbazovinylene)-1,1'-biphenyl ("BCzVBi") are suitable to attain cool white electroluminescence, although other doping concentrations can be used. Single-dopant devices with 30% v Pt(ptp)$_2$ give rise to a predominant dimer/excimer phosphorescence at longer wavelengths ($\lambda_{max}$~570 nm) concomitant with weak monomer phosphorescence ($\lambda_{max}$~476 nm), leading to a yellow-orange light output with (0.42, 0.53) CIE coordinates, which can then attain cool white light with color coordinates closer to the ideal (0.33, 0.33) CIE coordinates upon mixing with BCzVBi fluorescence ($\lambda_{ma}$~450 nm).

Figure 3:
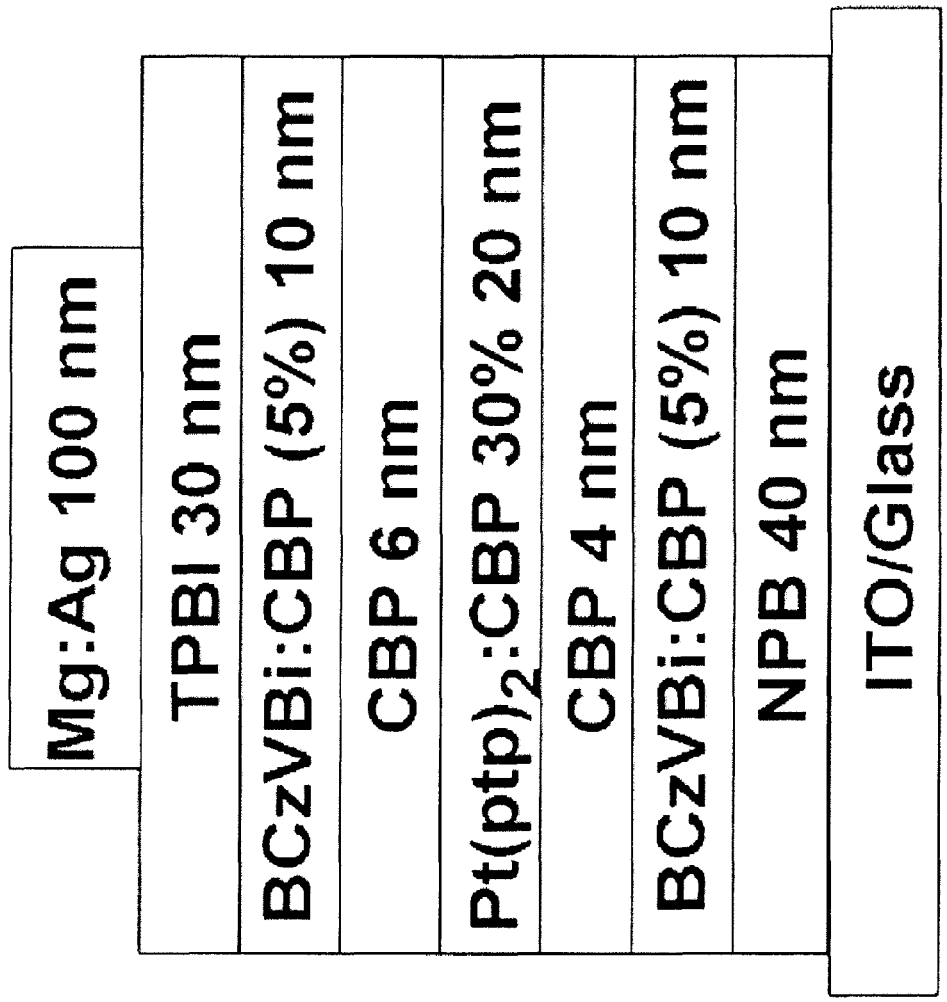
FIG. 3 shows the structure of an example of an improved cool WOLED.

The structure of an example of the improved cool WOLED device is shown in FIG. 3. The emissive layers are comprised of a yellow phosphorescent layer (20 nm) sandwiched between deep-blue fluorescent layers (10 nm on each side) in a common host separated by undoped spacer layers of the same host material. The dopants are Pt(ptp)$_2$ yellow phosphorescent and BCzVBi deep-blue fluorescent dopants. The host can be 4,4'-bis(carbazol-9-yl)biphenyl ("CBP"). The improved WOLED also includes a hole transporting layer that can be N,N'-diphenyl-N,N'-bis(1-naphthyl)-1,1'-biphenyl-4,4"-diamine ("NPB"), an electron transporting layer that can be 1,3,5-tris(phenyl-2-benzimidazolyl)-benzene ("TPBI"), a host and spacer material that can be CBP, a substrate that can be glass coated with photolithographically patterned indium-tin-oxide ("ITO"), and a cathode that can be Mg:Ag, LiF/Al, Ca/Al or Ca/Ag.

In particular, centrally located in one example of an improved cool WOLED structure is a yellow phosphorescent emissive layer made up of a host material that has been doped with a yellow phosphorescent dopant. The host material can be 4,4'-bis(carbazol-9-yl)biphenyl ("CBP"). The yellow phosphorescent dopant can be bis[3,5-bis(2-pyridyl)-1,2,4-triazolato]platinum(II) (Pt(ptp)$_2$). The yellow phosphorescent emissive layer can be approximately 20 nm in thickness.

On either side of the yellow phosphorescent emissive layer in one example of an improved cool WOLED structure can be layers of undoped host material. The host material in these spacer layers can be the same host material used in the yellow phosphorescent emissive layer. The host material can be CBP. The thickness of the spacer layers is determined by the Förster radius (~3 nm) (Ramos-Ortiz, 2002) to inhibit energy transfer from the blue fluorophore to the lower-energy phosphor. The thickness of the undoped spacer layers can be different. For example, the undoped spacer layer above the yellow phosphorescent emissive layer can be 6 nm thick and the undoped spacer layer below the yellow phosphorescent emissive layer can be 4 nm thick.

On either side of the undoped spacer layers in one example of an improved cool WOLED structure, and consequently on either side of the yellow phosphorescent emissive layer, can be deep-blue fluorescent emissive layers made up of a host material that has been doped with a deep-blue fluorescent dopant. The host material can be 4,4'-bis(carbazol-9-yl)biphenyl ("CBP"). The deep-blue fluorescent dopant can be 4,4'-(bis(9-ethyl-3-carbazovinylene)-1,1'-biphenyl ("BCzVBi"). The deep-blue fluorescent emissive layers can be approximately 10 nm in thickness. The doping concentration of the deep-blue fluorescent emissive layers can be approximately 5% by volume (v) of dopant to host material.

Below the lower deep-blue fluorescent emissive layer in one example of an improved cool WOLED structure can be a hole transporting layer. The hole transporting layer can be made up of N,N'-diphenyl-N,N'-bis(1-naphthyl)-1,1'-biphenyl-4,4"-diamine ("NPB"). The hole transporting layer can be about 40 nm in thickness. Improved performance can be achieved in one example by adding a film of N,N'-dicarbazolyl-3,5-benzene ("mCP"), which can be about 10 nm thickness, on top of the NPB layer, or in another example by replacing both NPB and mCP by 1,1-bis-(4-bis(4-methylphenyl)-amino-phenyl)-cyclohexane ("TPAC").

Above the higher deep-blue fluorescent emissive layer in one example of an improved cool WOLED structure can be an electron transporting layer. The electron transporting layer in this example WOLED structure can be made up of 1,3,5-tris(phenyl-2-benzimidazolyl)-benzene ("TPBI") that can be 40 nm in thickness. In other examples the TPBI can be replaced by other electron-transporting materials such as tris(2,4,6-trimethyl-3-(pyridin-3-yl)phenyl)borane ("3TPYMB" or "TPYMB"), 1,3,5-tris(m-pyrid-3-yl-phenyl)benzene ("TmPyPB"), 1,3,5-tris(p-pyrid-3-yl-phenyl)benzene ("TpPyPB"), or 4,7-diphenyl-1,10-phenanthroline ("BPhen"), and other suitable materials.

As in standard OLED devices, the improved WOLED devices also include a substrate material and a cathode.

EXAMPLE 1

Synthesis of Pt(ptp)$_2$

The synthesis of the ligand ptp (3,5-bis(2-pyridyl)-1,2,4-triazolate) was based on a procedure described in the literature (Bentiss et al., 2002). To synthesize the Pt(ptp)$_2$ complex, 0.4500 g of the ptp ligand was suspended in pyridine in a round bottom flask and then heated in an oil bath until the solid dissolved completely. To the resulting solution of the ptp ligand was slowly added another solution of 0.4700 g of the metal precursor cis-bis(benzonitrile)dichloroplatinum(II) in acetone. The reaction was maintained at 50-60° C. for three days. The final product was obtained as a yellow powder with 65% yield of Pt(ptp)$_2$.

Figure 4:
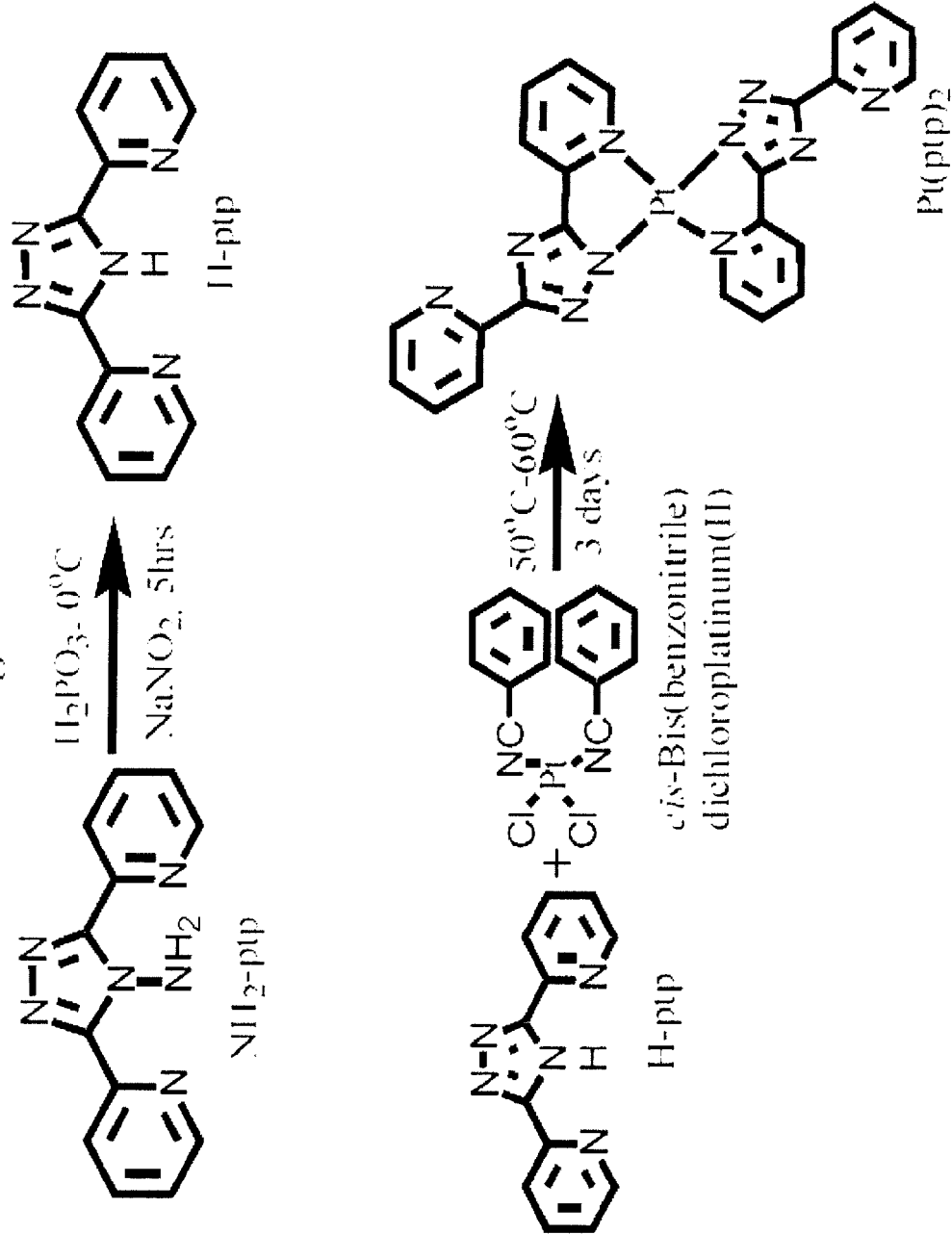
FIG. 4 shows a general scheme for the synthesis of Pt(ptp)$_2$.

The resultant compound demonstrated poor solubility in most solvents; the best solvent system used was a mixture of dichloromethane and methanol. Yellow crystals with green PL formed by slow evaporation of a solution of Pt(ptp)$_2$ in this solvent mixture at room temperature. X-ray analysis showed that the yellow form of Pt(ptp)$_2$ contained methanol solvate while drying the material under vacuum led to a non-solvated orange form that also exhibited orange PL. FIG. 4 summarizes the synthesis of the Pt(ptp)$_2$ embodiment.

EXAMPLE 2

Photoluminescence Properties of Thin Films

Figure 5:
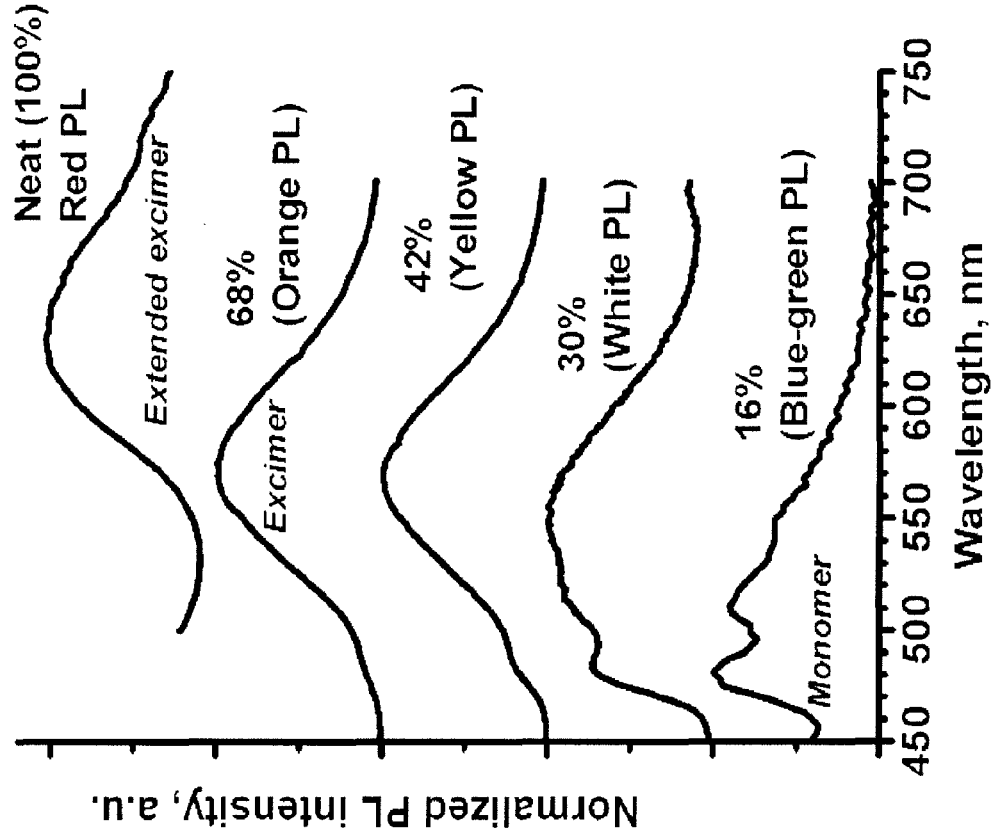
FIG. 5 shows the PL spectra of x % Pt(ptp)$_2$:CBP thin films deposited by co-sublimation.

FIG. 5 shows the PL properties of thin films of Pt(ptp)$_2$ in the common OLED host CBP. FIG. 5 shows the PL spectra of particular percentages of Pt(ptp)$_2$:CBP thin films. The films were made by co-deposition of Pt(ptp)$_2$ and CBP via thermal evaporation (sublimation) of pure powder samples of both compounds in a Trovato organic deposition system onto glass substrates. The monomer and excimer bands are combined. The data in FIG. 5 demonstrate that white light in the functional thin film form of OLEDs is achieved by controlling the doping level of Pt(ptp)$_2$ in CBP, which is significant for SSL. White light is achieved for the 20-30% volume Pt(ptp)$_2$:CBP doped film due to the combination of the blue monomer emission and the orange excimer emission. The data in FIG. 5 also show that the emission color can be tuned intuitively between blue and red simply by varying the doping level of Pt(ptp)$_2$ in CBP. These PL data can act as a backdrop to guide the design of white and monochrome OLEDs.

EXAMPLE 3

Electroluminescence Data

Figure 6:
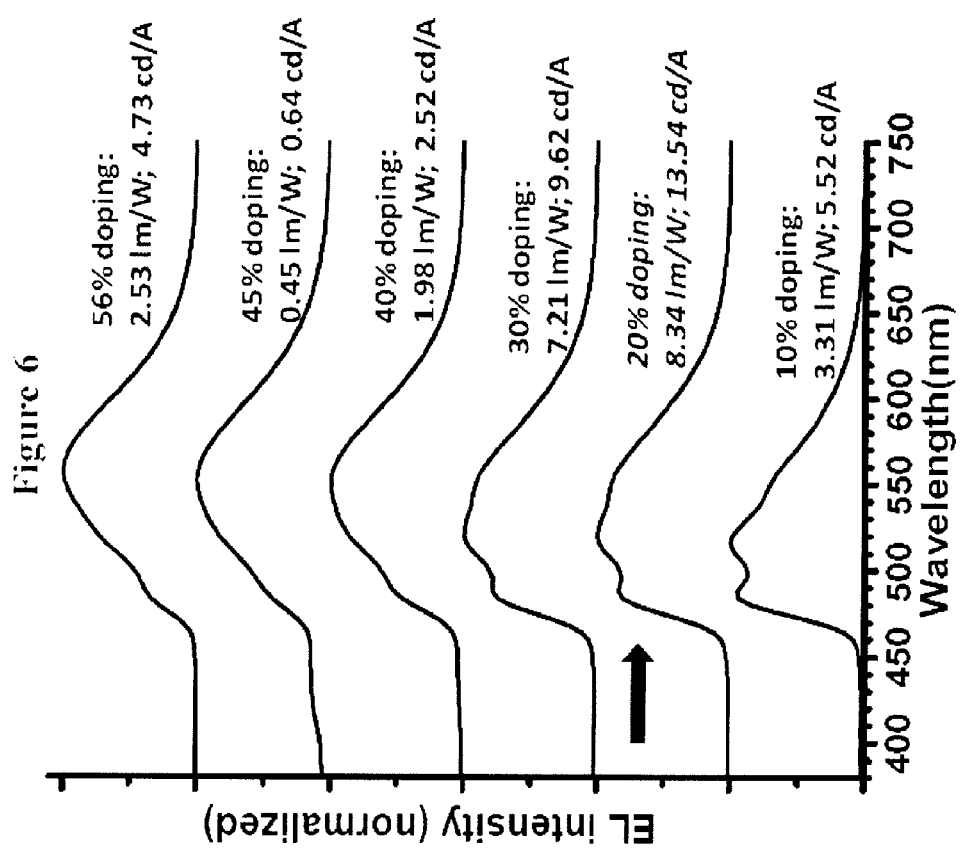
FIG. 6 shows the EL spectra for multi-layer OLEDs based on x % Pt(ptp)$_2$:CBP emissive layer.

FIG. 6 shows representative EL data for OLEDs based on Pt(ptp)$_2$:CBP as an emitting layer in a standard device structure. The device structure is the same in all devices, i.e., ITO/NPB (40 nm)/xvolume % Pt(ptp)$_2$:CBP (25 nm)/TPBI (30 nm)/Mg:Ag.

The EL spectra in FIG. 6 clearly mirrors the PL spectra in FIG. 5 in terms of the ability to tune the emission colors by varying the doping level. The best device shown in FIG. 5 that exhibits white electrophosphorescence has a maximum power efficiency of 8.34 lm/W and maximum luminance efficiency of 13.54 cd/A. These values represent a lower limit for this material because devices were made with less-than-idealized conditions (e.g., no cleanroom or in situ conditions, imperfect substrate treatment, non-sublimed dopant, and unoptimized device structure). For example, standard baseline devices that utilize the well-known Ir(ppy)$_3$:CBP system as emissive layer with the same device structure as the one used for Pt(ptp)$_2$:CBP devices have attained 40-50% of the performance for devices reported in the literature under optimized conditions, and other device structures are known to lead to even higher performance.

The performance parameters for Pt(ptp)$_2$-based devices can be dramatically improved to achieve power efficiencies of 20-100 lm/W by improving the charge balance and further optimization in the device structure. Doing so has led to an order-of-magnitude increase in power efficiencies vs. FIG. 6 data, including in one example 25-30 lm/W for the orange OLEDs with 40-80% Pt(ptp)$_2$:CBP attained simply by adding a 10-nm thin layer of mCP as an electron- and exciton-blocking layer. In another example 30-40 lm/W was attained for the orange-red OLEDs with neat emissive layers of Pt(ptp)$_2$ by changing NPB to TPAC and changing TPBI to TPYMB. In a third example 60-70 lm/W was attained for blue-green OLEDs with 1-10% doping levels of Pt(ptp)$_2$ made by other changes in the device structure including the host and cathode materials. These results represent much better performance than the previous literature precedents for devices based on Pt complexes that exhibit monomer and excimer electrophosphorescence (D'Andrade, 2002; D'Andrade, 2004; Williams, 2007; Brooks, 2002; Yang, *Adv. Mater.* 2008; Yang, *Appl. Pys. Lett.* 2008; Ma, 2006). Two other major advantages, besides higher maximum power efficiencies, for monochrome and white OLEDs based on Pt(ptp)$_2$ compared to these literature precedents are: (i) no significant shift in the emission profile with voltage, current density, or brightness whereas a severe shift in the monomer/excimer peak ratio was obtained in the aforementioned literature precedents, and (ii) the devices are generally more stable at high current density compared to not only the aforementioned literature precedents but also to electrophosphorescent OLEDs in general including those based on 14111) phosphorescent dopants such as Ir(ppy)$_3$ or FIrpic.

EXAMPLE 4

X-Ray Structural Data

Figure 7:
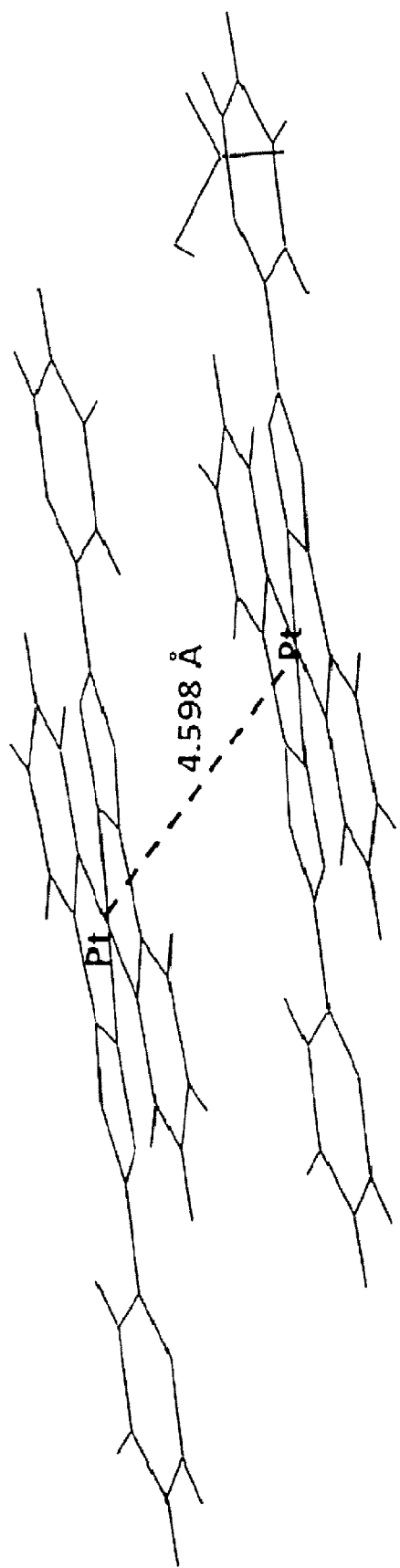
FIG. 7 shows the crystal structures of the solvated form (a), top, and dry form (b), bottom, of Pt(ptp)$_2$.

Crystals of the Pt(ptp)$_2$ complex exhibit two polymorphs with different packing forms: (a) solvated yellow crystals, and (b) dry orange crystals. While form (a) has the molecules arranged as poorly-overlapping, offset adjacent molecular units and contains a solvent (methanol) molecule that is H-bonded to the complex, form (b) has extended linear chains of strongly overlapping stacked complexes and short Pt—Pt intermolecular distances (3.289 Å). FIG. 7 shows the structural data for both forms. The PL properties are different for the two polymorphs. The yellow form (a) has blue-green emission due to monomers while the orange form (b) has orange-red emission due to extended excimers. In addition to facilitating the assignment of the PL and EL bands, the X-ray structural data also suggest a conducting or semiconducting behavior for Pt(ptp)$_2$ and like complexes due to the close stacking of the Pt centers in the dry form. As well, since pyridyl(triazolate) ligands in general and the ptp ligand in particular are rather electron poor, the conductivity is unipolar and selective for electrons instead of holes. The combination of this unipolar property and the extended structure render square-planar pyridyl(triazolate) complexes ideal for use as n-type semiconductors in organic field-effect transistors (OFETs)—also known as organic thin film transistors (OTFTs), which are the central components of electronic devices.

FIG. 1 shows the general chemical structure of this class of complexes. Varying the metal (M) or the substituent (R) allows control of the extent of the n-type conducting behavior and/or facilitates the deposition of the materials into the functional thin film form needed for the devices by either thermal evaporation (sublimation) of solids or casting from solution (spin coating or inkjet printing).

EXAMPLE 5

Device Fabrication

Devices were fabricated on photolithographically patterned ITO (~20 Ω/sq) substrates cleaned and pretreated in $O_2$ plasma at 300 W for 10 minutes prior to deposition of organic layers. All organic molecules were purchased as high-purity reagents from H. W. Sands Corp. (Jupiter, Fla.) or Lumtec Corp. (Taiwan) and used as received without further purification while the phosphorescent complex was synthesized as described in U.S. Provisional Patent Application No. 61/188,428. The organic stack was deposited at <1 Å/s without breaking vacuum ($7 \times 10^{-7}$ Torr). The Mg:Ag cathode, ~100 nm thick, was thermally evaporated to cap the organic layers and the devices were sealed immediately in an $N_2$-purged glove box prior to electrical characterization.

EXAMPLE 6

Electroluminescence Properties—Cool WOLEDS

Figure 8:
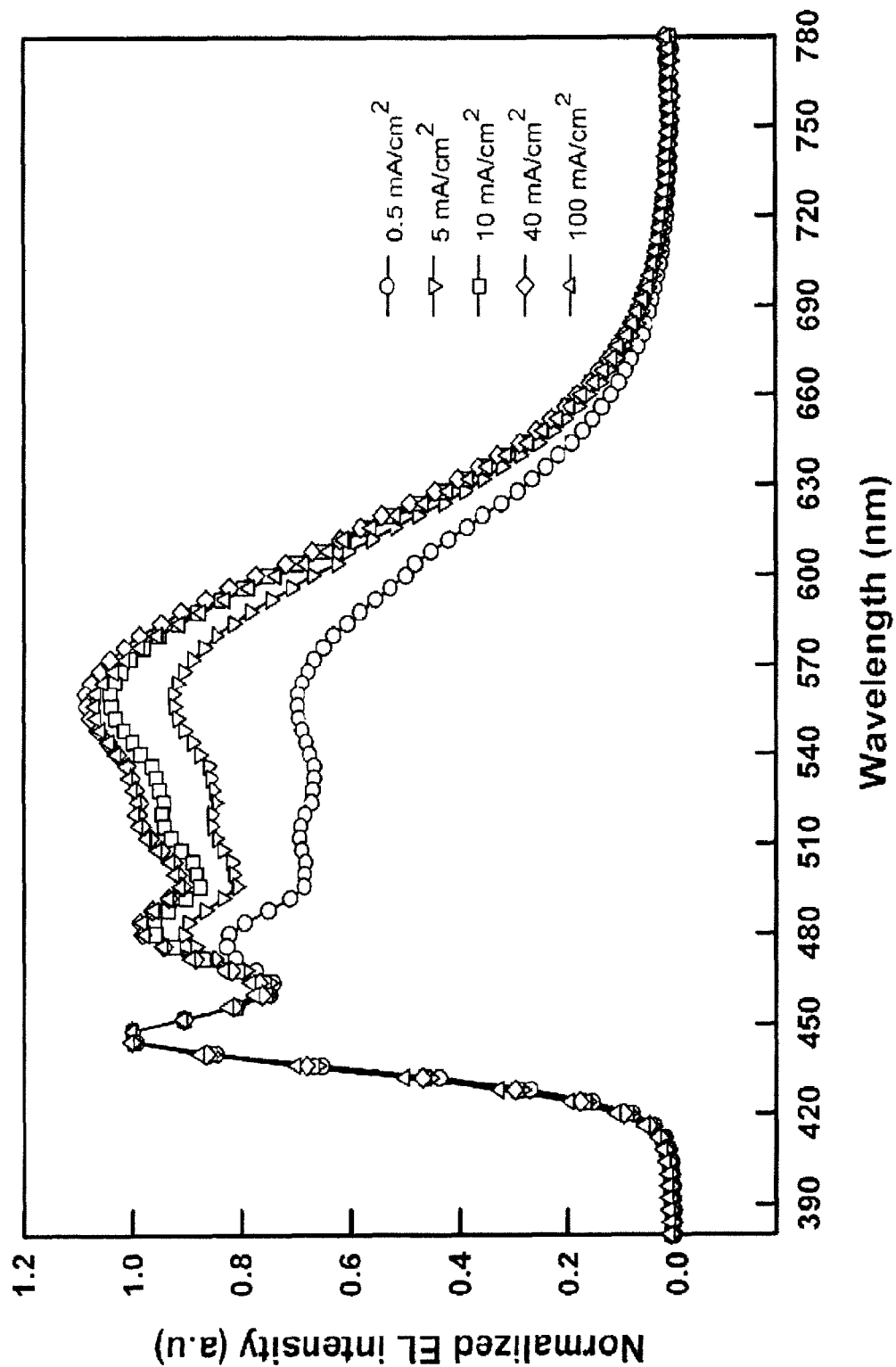
FIG. 8 shows normalized EL spectra vs. current density for an example of an improved cool WOLED.

FIG. 8 shows the electroluminescence ("EL") spectra of an example of an improved cool WOLED. The varying relative emission intensities of BCzVBi and $Pt(ptp)_2$ suggests expansion of the recombination zone from the fluorophore-doped regions at lower current densities into the phosphor-doped layer at higher operating bias or current, causing slight changes in the EL spectra and CIE coordinates.

Figure 9:
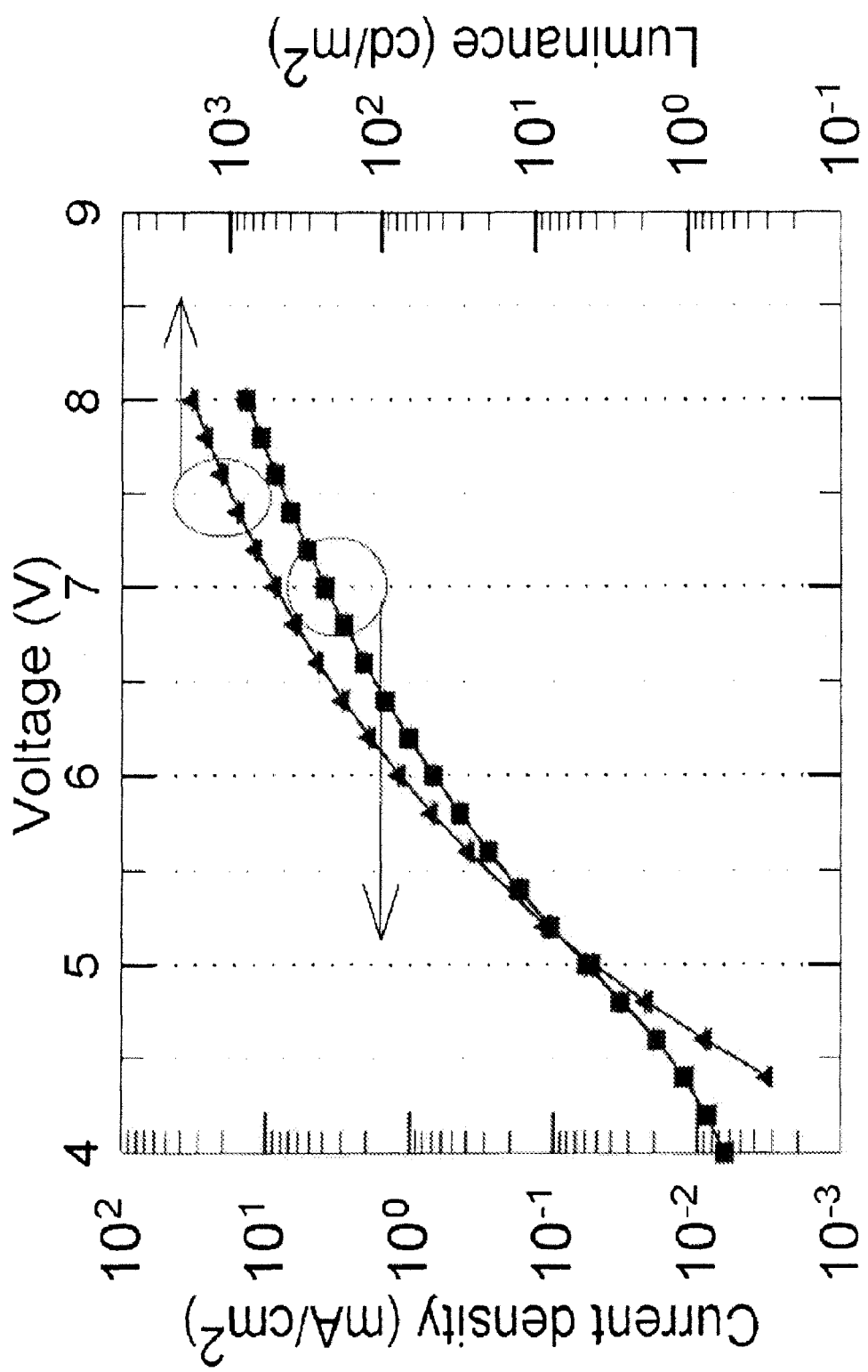
FIG. 9 shows the variation of current density (squares; left y-axis indicated by circle and left arrow) and luminance (triangles; right y-axis indicated by circle and right arrow) versus voltage (x-axis) for an example of an improved cool WOLED.
Figure 10:
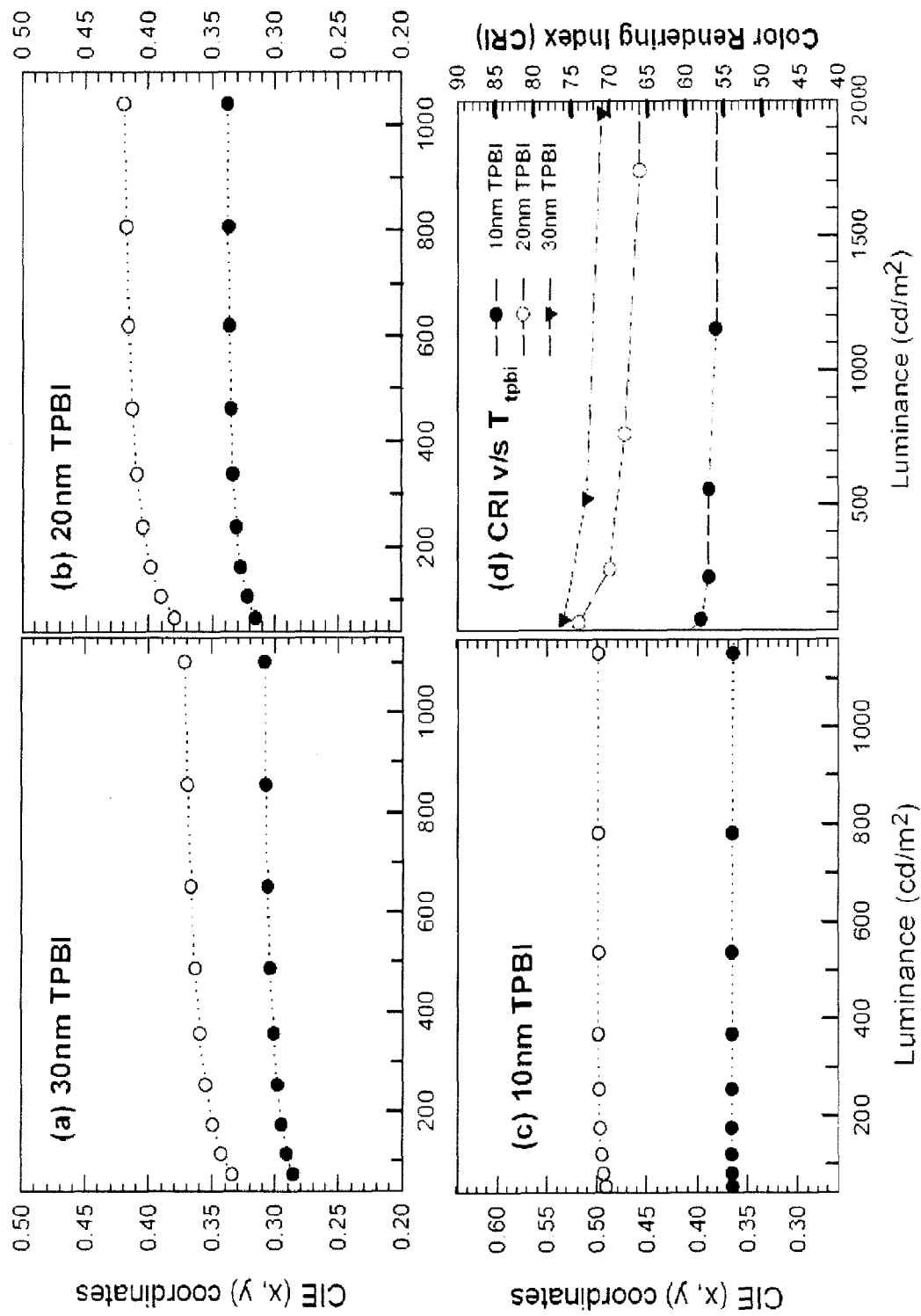
FIG. 10 shows CIE and CRI vs. luminance upon varying the thickness of the electron transport layer (TPBI) for an example of an improved cool WOLED.

FIG. 9 shows the current density-voltage-luminance (J-V-L) characteristics of this example of a cool WOLED. The devices show increased BCzVBi emission upon systematic increase in the ETL thickness. FIG. 10 shows the consequent optimization of CIE coordinates vs. brightness upon varying TPBI thickness in this example. More efficient exciton confinement and charge balance through addition of suitable organic layers may further optimize efficiency metrics.

The power efficiency (P.E.), luminous efficiency (L.E.) and the external quantum efficiency (EQE) are also higher for the improved WOLED with 30 nm instead of thinner ETL, as shown in Table 1 below. Table 1 shows a summary of device characteristics for a WOLED with 30 nm TPBI. The device structure is shown in FIG. 3.

TABLE 1

| Brightness (cd · m$^{-2}$) | Bias (V) | J (mA · cm$^{-2}$) | P.E. (lm · W$^{-1}$) | L.E. (cd · A$^{-1}$) | CRI | CIE (x, y) | EQE (%) |
| --- | --- | --- | --- | --- | --- | --- | --- |
| 50 ± 2 | 5.8 | 0.44 ± 0.02 | 5.7 ± 0.1 | 10.6 ± 0.2 | 76 | (0.28, 0.32) | 4.8 |
| 100 ± 5 | 6.2 | 1.00 ± 0.05 | 6.0 ± 0.1 | 11.8 ± 0.2 | 76 | (0.29, 0.34) | 5.2 |
| 500 ± 15 | 7.0 | 3.90 ± 0.15 | 5.8 ± 0.1 | 12.9 ± 0.2 | 73 | (0.30, 0.36) | 5.4 |
| 1100 ± 25 | 7.6 | 8.60 ± 0.25 | 5.4 ± 0.1 | 13.0 ± 0.2 | 72 | (0.30, 0.37) | 5.3 |

The stability of all performance parameters shown in Table 1 is striking. Thus, the power and luminous efficiencies, CRI, and external quantum yield at the operational condition of ~4000 cd/m$^2$ in the WOLED are at 94%, 123%, 95%, and 110% of their corresponding highest values at low brightness near turn-on voltages. This stability is better than that in other all-phosphor or even fluorophore/phosphor WOLED precedents, suggesting that triplet-triplet annihilation processes that normally degrade electrophosphorescent devices are not as significant in the $Pt(ptp)_2$-containing WOLEDs herein.

EXAMPLE 7

Electroluminescence Properties—Warm WOLEDS

Figure 11:
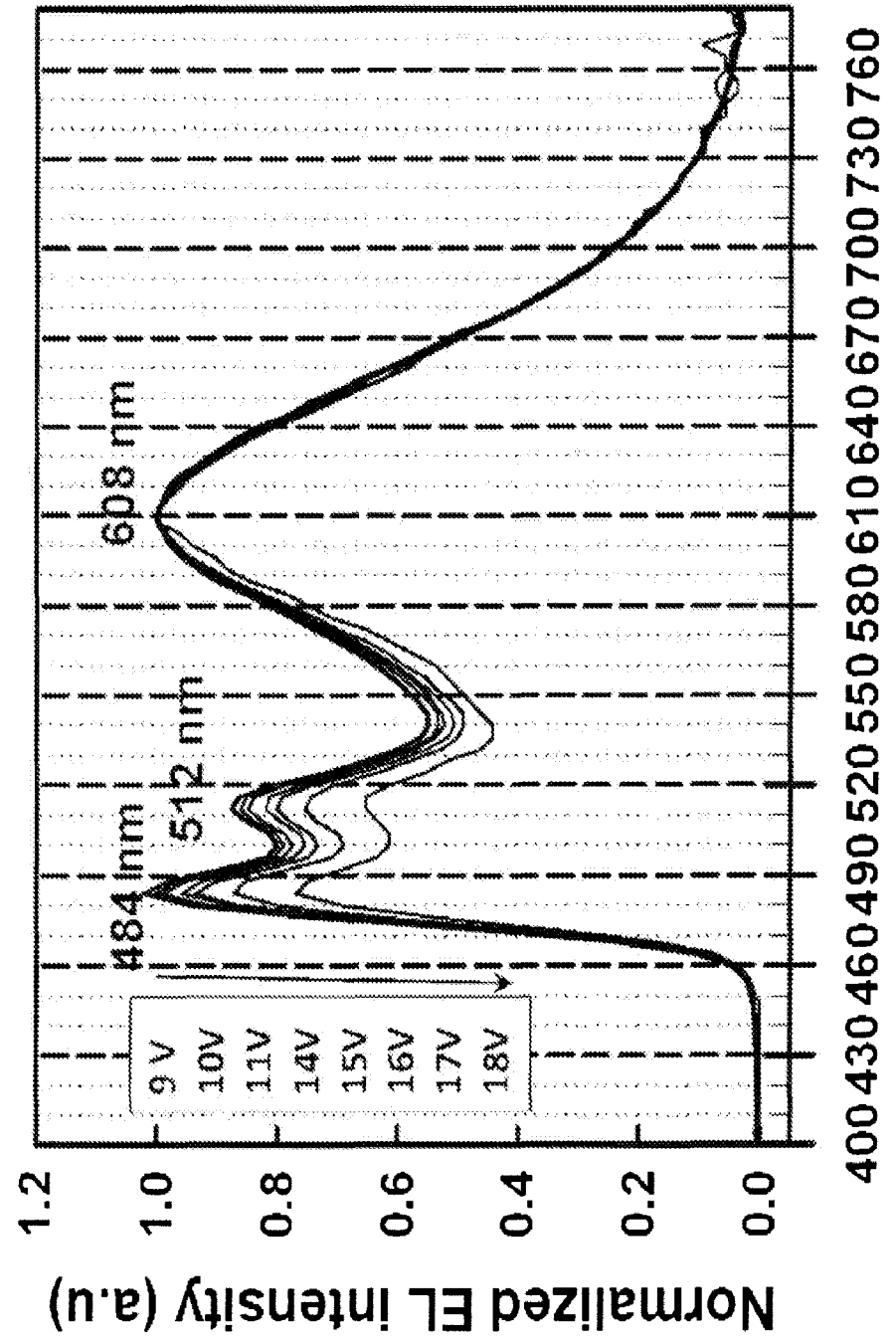
FIG. 11 shows EL spectra vs. voltage for an example of an improved warm WOLED that utilizes only a single emitter, Pt(ptp)$_2$, in two different emission regions.

FIG. 11 shows EL spectra vs. voltage for an example of an improved warm WOLED that utilizes only a single emitter, $Pt(ptp)_2$, in two different emission regions. The device structure includes NPB as a hole transporting layer, mCP as an electron- and exciton-blocking layer, TPBI as an electron transporting layer, CBP as host for one emissive layer doped with 5% $Pt(ptp)_2$ phosphorescent dopant, and another emissive layer consisting of a neat film of $Pt(ptp)_2$. The CRI is up to 82 with excellent color stability for such devices.

Further improvement of device performance and/or color quality of such warm WOLEDs can be attained by means that include changing the thickness of the neat or doped films in the two emissive layers, altering the positioning of the two emissive layers, replacing the neat film by a highly-doped film with for example >30% doping levels, small variations in the doping level of the lightly-doped film for example within 1-10% doping levels, changing the host from CBP to other hosts, changing the Mg:Ag cathode to LiF/Al or other low work function cathodes, and altering the materials and/or thicknesses of other layers in the device besides the emissive layers. These strategies produce improvements in device performance and fine tuning of white color coordinates and CRI.

EXAMPLE 8

Device Optimization—Monochrome and Near-White Doping-Based OLEDS

Monochrome, near-white and white OLEDs based on the $Pt(ptp)_2$ embodiment can be partially optimized by improving the charge balance in the devices, which is attainable by varying the materials and/or thicknesses comprising each device layer. Full optimization is a laborious task but the multiple examples below demonstrate the vast improvement in device performance upon partial optimization of the architecture of various OLED types based on $Pt(ptp)_2$.

Figure 12:
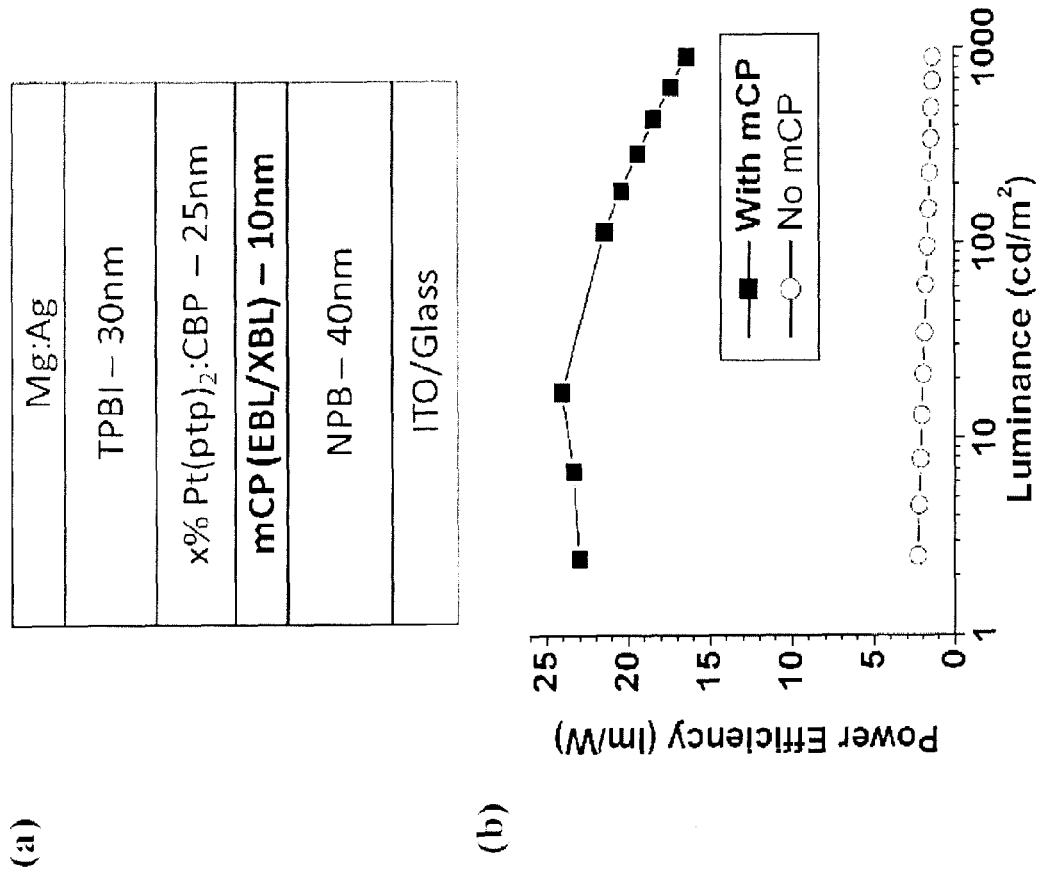
FIG. 12 shows (a) the device structure and (b) power efficiency vs. luminance in an example of partial optimization of the performance of OLEDs based on Pt(ptp)$_2$ doped in CBP upon addition of a thin film of the exciton and electron blocking material mCP.

FIG. 12 shows (a) structure and (b) power efficiency vs. luminance for an example of a partially optimized OLED, with partial optimization of the performance of OLEDs based on $Pt(ptp)_2$ doped in CBP upon addition of a 10-nm thin film of "mCP" as an electron/exciton blocking layer (EBL/XBL). Devices with other X % $Pt(ptp)_2$:CBP doping levels produced power efficiencies of approximately 20-50 lm/W upon this partial optimization and most devices that utilized in this general device structure showed very little efficiency roll-off at high brightness. Even higher performance is anticipated upon further optimization of the device architecture.

EXAMPLE 9

Device Optimization—Cool WOLEDS

Figure 13:
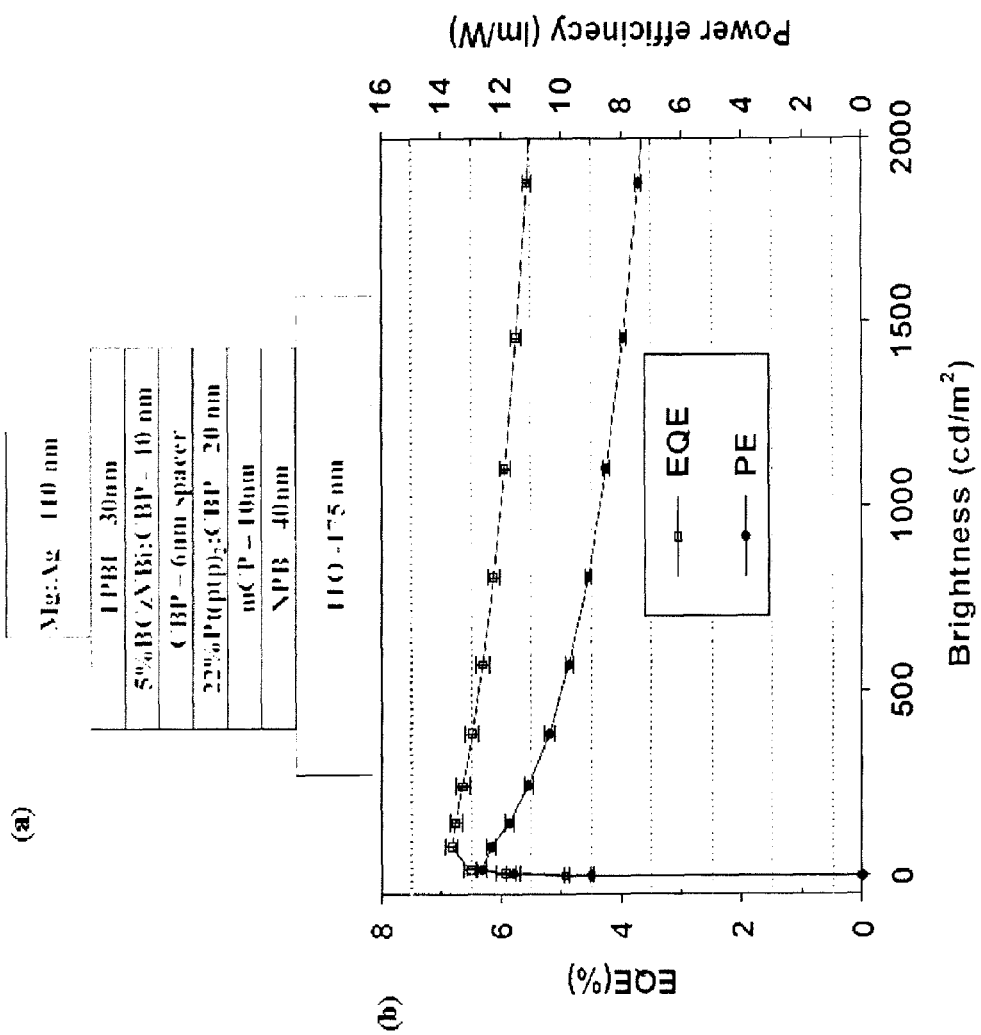
FIG. 13 shows (a) the device structure and (b) a plot of power efficiency (PE) and external quantum efficiency (EQE) for a partially-optimized cool WOLED based on a fluorophore/phosphor combination of two emitters.

FIG. 13 shows that further improvement in the EL device performance of the example cool WOLED can be achieved upon improving the device structure by adding a thin film of the electron and exciton blocking material "mCP". Thus, the power efficiency (PE) and external quantum efficiency (EQE) shown in FIG. 13(b) have nearly doubled upon this partial optimization using the device structure in FIG. 13(a) compared to the device structure in FIG. 3.

Further improvement of device performance and/or color quality of such cool WOLEDs can be attained by means that include varying the material or doping level of the deep-blue fluorophore layers, varying the doping level of the $Pt(ptp)_2$ in the CBP host, replacing the doped $Pt(ptp)_2$: CBP film by a neat film of $Pt(ptp)_2$, changing the thickness of the fluorophore or phosphor films, changing the common host from CBP to other hosts, changing the Mg:Ag cathode to LiF/Al or other low work function cathodes, and altering the materials and/or thicknesses of other layers in the device besides the emissive layers. These strategies have led to improvements in device performance and fine tuning of white color coordinates and CRI, as demonstrated below for other OLED device types based on $Pt(ptp)_2$.

EXAMPLE 10

Device Optimization—Warm WOLEDS

Figure 14:
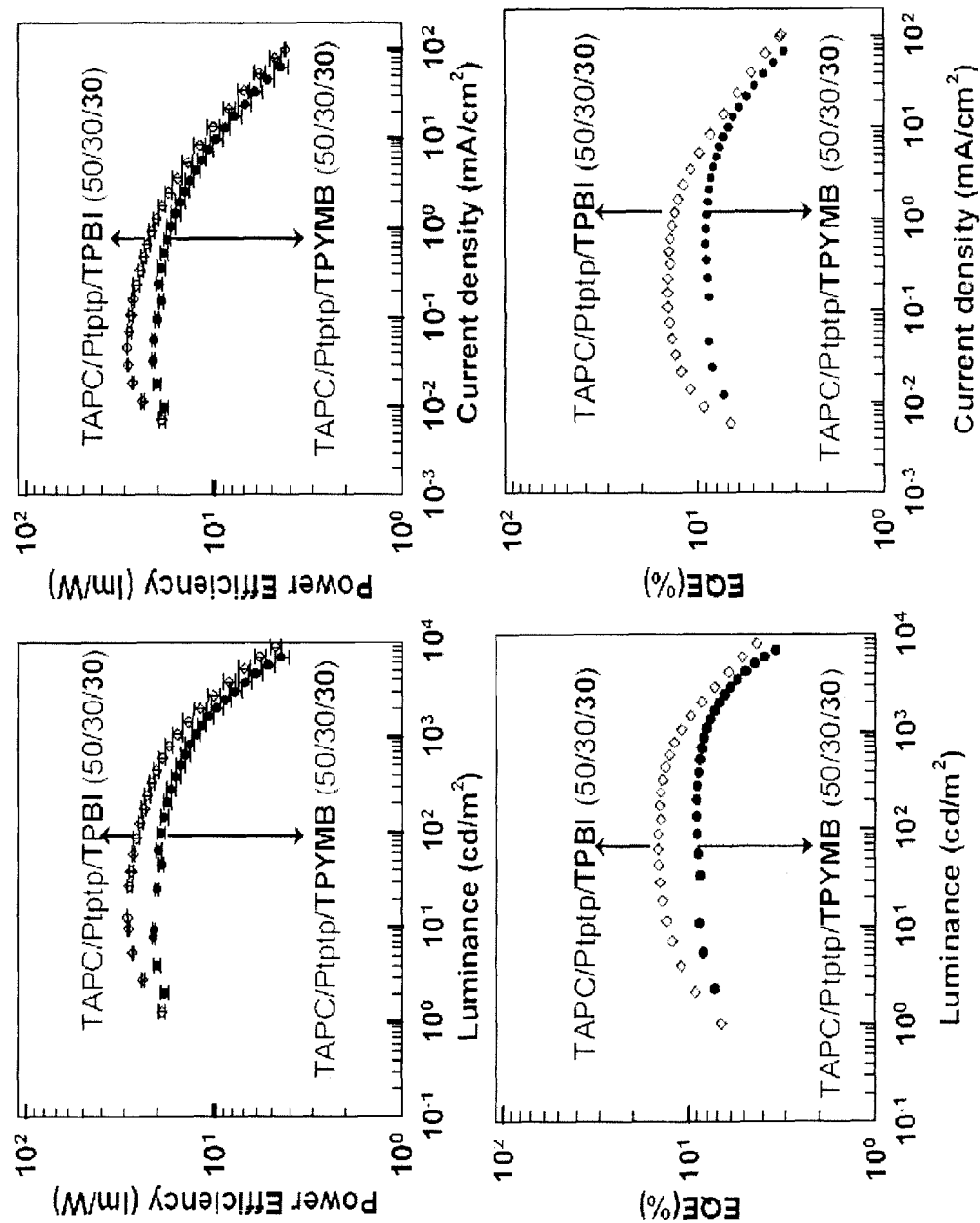
FIG. 14 shows plots of power efficiency and EQE for a partially-optimized OLED based on a neat emissive layer of Pt(ptp)$_2$ upon changing the hole transporting material from NPB to TPAC and the electron transporting material from TPBI to TPYMB.
Figure 15:
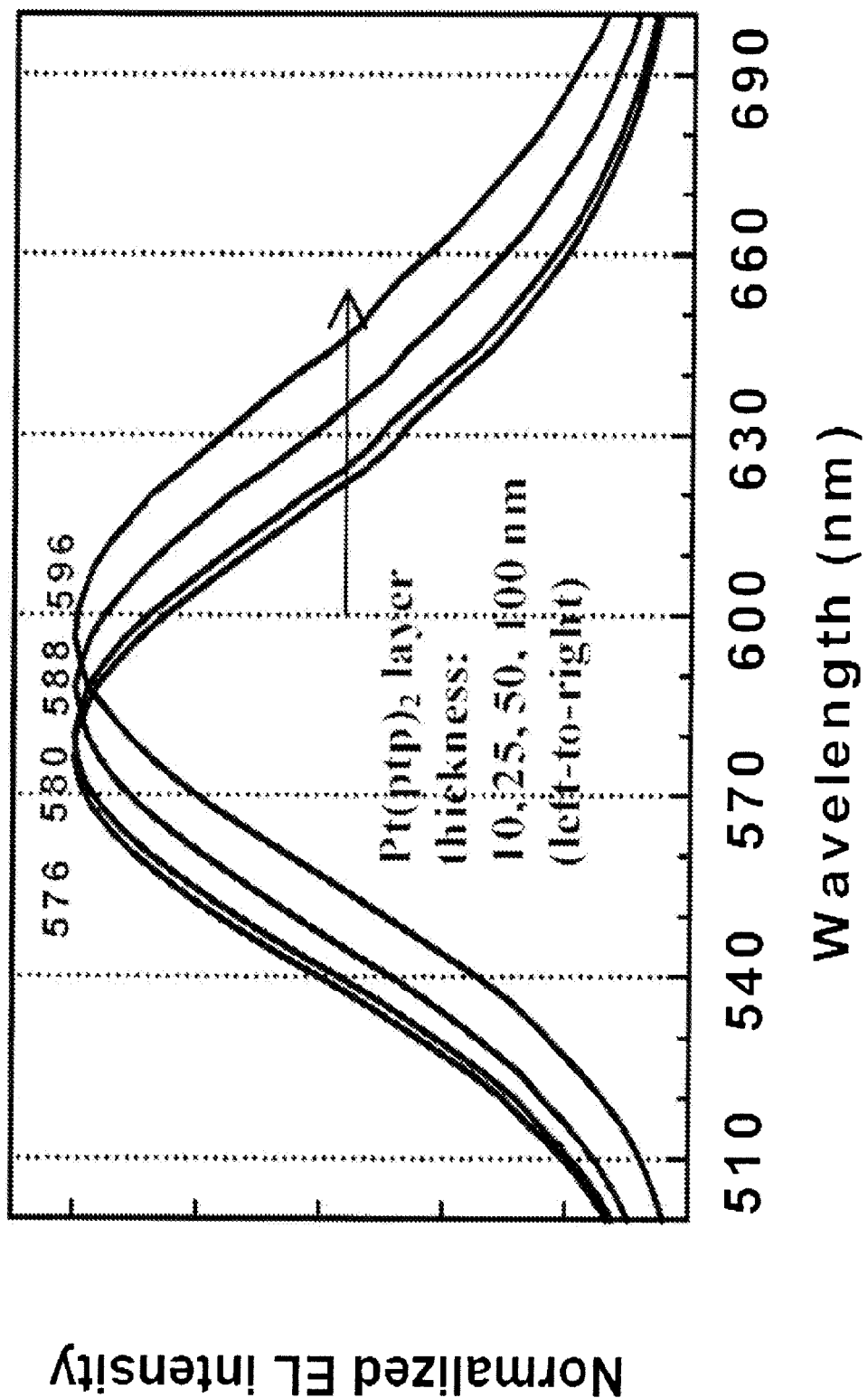
FIG. 15 shows normalized EL intensity vs. wavelength from color tuning of OLEDs by changing the thickness of the neat emissive layer of Pt(ptp)$_2$.

Warm WOLEDs based on $Pt(ptp)_2$ as a single emitter in one or two emissive layers can be optimized by changes in the device structure. FIGS. 14-15 illustrate two examples for this optimization for devices based on a single emissive layer of neat $Pt(ptp)_2$. The same principle is applicable to warm WOLEDs with higher CRI that are based on $Pt(ptp)_2$ as a single emitter in two emissive layers. FIG. 14 shows plots of power efficiency and external quantum efficiency (EQE) for a partially-optimized OLED based on a neat emissive layer of $Pt(ptp)_2$. The partial optimization has been achieved by modifying the baseline device structure upon changing the hole transporting material from NPB to TPAC and changing the electron transporting material from TPBI to TPYMB. Although devices based on neat films are rather inefficient (~3 lm/W) in the baseline structure with NPB as HTL and TPBI as ETL, an order of magnitude increase in power efficiency is achieved upon improving the charge balance in the devices by using the alternative materials.

FIG. 15 demonstrates color tuning of OLEDs made from a single emissive layer by changing the thickness of the neat emissive layer of $Pt(ptp)_2$. FIG. 15 shows normalized EL intensity vs. wavelength, with half-maximum wavelengths varying versus thickness according to Table 2 below.

TABLE 2

| Thickness $Pt(ptp)_2$ | λ (nm) at half maximum |
|---|---|
| 10 nm | 628-532 |
| 25 nm | 632-536 |
| 50 nm | 640-540 |
| 100 nm | 652-552 |

Thus, the peak maximum and full width at half maximum can be controlled by changes in the thickness of the emissive layer. Further improvement in the color coordinates and device efficiency can be attained by following the same strategies described above.

REFERENCES CITED

The following documents and publications are hereby incorporated by reference.

U.S. PATENT DOCUMENTS

U.S. Provisional Patent Application No. 61/188,428
U.S. Provisional Patent Application No. 61/176,190

OTHER PUBLICATIONS

Brooks, J., Y. Babayan, S. Lamansky, P. I. Djuorvich, I. Tsyba, R. Bau and M. E. Thompson, *Inorg. Chem.*, 41, 3055 (2002).
D'Andrade, B. W.; Adamovich, V.; Thompson, M. E.; Forrest, S.; *Adv. Matt.* 14, 1032 (2002).
D'Andrade, B. W., R. J. Holmes, S. R. Forrest, *Adv. Mater.* 16, 624 (2004).
Kanno, H., N. C. Giebink, Y. Sun and S. R. Forrest, *Appl. Phys. Lett.* 89, 023503 (2006).
Ma, B. W., P. I. Djurovich, S. Caron, B. Alleyne, and M. E. Thompson, *Adv. Funct. Mater.*, 16, 2438 (2006).
Misra, A.; Kumar, P.; Kamalasanan, M. N.; Chandra, S. "White organic LEDs and their recent advancements", *Semicond. Sci. Technol.* 21, R35R47 (2006).
Newman, C. R.; Frisbie, C. D.; da Silva Filho, D. A.; Bredas, J.-L.; Ewbank, P. C.; Mann, K. R. "Introduction to Organic Thin Film Transistors and Design of n-Channel Organic Semiconductors" *Chem. Mater.* 16, 4436 (2004).
Qi, X., M. Slootsky, and S. R. Forrest, *Appl. Phys. Lett.* 93, 193306 (2008).
Ramos-Ortiz, G., Y. Oki, B. Domercq and B. Kippelen, *Phys. Chem. Chem. Phys.*, 4, 4109 (2002).
Sun, Y., N. C. Giebink, H. Kanno, B. Ma, M. E. Thompson & S. R. Forrest, *Nature*, 908 (2006).
Williams, E. L., K. Haavisto, J. Li, and G. E. Jabbour, *Adv. Mater.* 19, 197 (2007).
Wu, Y. Z., X. Y. Zheng, W. Q. Zhu, R. G. Sun, X. Y. Jiang, Z. L. Zhang, and S. H. Xu, *Appl. Phys. Lett.*, 83, 5077 (2003)
Yang, X., Z. Wang, S. Madakuni, J. Li, and G. E. Jabbour, *Adv. Mater.*, 20, 2405 (2008).
Yang, X., Z. Wang, S. Madakuni, J. Li, and G. E. Jabbour, *Appl. Phys. Lett.* 93, 193305 (2008).

What is claimed is:

1. Homoleptic square planar complexes having the general structure:

$$[M(N^\wedge N)_2],$$

wherein M is a metal center, N^N is 3,5-bis(2-pyridyl)-1,2,4-triazolate, and wherein two identical 3,5-bis(2-pyridyl)-1,2,4-triazolate ligands are coordinated to M.

2. Organic light emitting diodes ("OLEDs") comprising one or more emissive layers, wherein at least one of the emissive layers comprises the homoleptic square planar complexes of claim 1.

3. A sensor comprising the homoleptic square planar complexes of claim 1, wherein the sensor is for sensing temperature, pressure, metal ions, or pH.

4. Organic thin film transistors ("OTFTs") comprising the homoleptic square planar complexes of claim 1.

5. The organic thin film transistors ("OTFTs") of claim 4, wherein the OTFTs are n-type OTFTs.

6. Complementary metal-oxide semiconductor ("CMOS") devices comprising the organic thin film transistors ("OTFTs") of claim 4.

7. A method for preparing a white organic light emitting diode ("WOLED") comprising:
doping one or more emissive layers with an amount of the homoleptic square planar complexes of claim 1.

8. Bidentate square planar complexes of triazolates having the general structure:

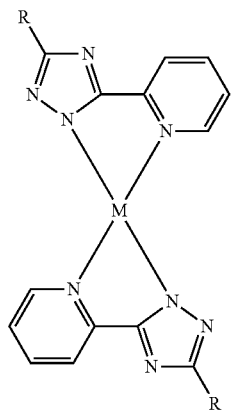

wherein:
M is Pt; and
R is pyridyl.

9. White organic light emitting diodes ("WOLEDs") comprising one or more emissive layers, wherein at least one of the emissive layers comprises the bidentate square planar complexes of triazolates of claim 8.

10. The white organic light emitting diodes ("WOLEDs") of claim 9, wherein at least one of the emissive layers comprises a host material and wherein at least one of the emissive layers consists of only the bidentate square planar complexes of triazolates of claim 8.

11. The white organic light emitting diodes ("WOLEDs") of claim 9, wherein the one or more emissive layers further comprise a host material.

12. The white organic light emitting diodes ("WOLEDs") of claim 11, wherein the host material comprises 4,4'-bis(carbazol-9-yl)biphenyl ("CBP"), 4,4'-Bis(9-carbazolyl)-2,2-Dimethyl-biphenyl ("CDBP"), N,N'-dicarbazolyl-3,5-benzene ("mCP"), 4,4',4"-tris(N-carbazolyl)triphenylamine ("TCTA"), or combinations thereof.

13. The white organic light emitting diodes ("WOLEDs") of claim 11, wherein the bidentate square planar complexes of triazolates of claim 9 are doped in the host material in the one or more emissive layers in different amounts per layer.

14. The white organic light emitting diodes ("WOLEDs") of claim 9, wherein the one or more emissive layers further comprise one or more additional fluorescent or phosphorescent emitting materials.

15. The white organic light emitting diodes ("WOLEDs") of claim 14, wherein the bidentate square planar complexes of triazolates of claim 8 and the one or more additional fluorescent or phosphorescent emitting materials are present together in at least one emissive layer.

16. The white organic light emitting diodes ("WOLEDs") of claim 14, wherein at least one of the emissive layers comprises a host material doped with the one or more additional fluorescent or phosphorescent emitting materials and wherein at least one of the emissive layers consists of only the bidentate square planar complexes of triazolates of claim 8.

17. A method for preparing a white organic light emitting diode ("WOLED") comprising:
doping one or more emissive layers with an amount of the bidentate square planar complexes of triazolates of claim 8.

18. A white organic light emitting diode ("WOLED"), comprising:
two deep-blue fluorescent emissive layers comprising a deep-blue fluorescent dopant; and
a yellow phosphorescent emissive layer comprising bis[3,5-bis(2-pyridyl)-1,2,4-triazolato]platinum(II) ("Pt(ptp)$_2$"),
wherein the yellow phosphorescent emissive layer is located between the two deep-blue fluorescent emissive layers.

19. The white organic light emitting diode ("WOLED") of claim 18, wherein the deep-blue fluorescent dopant is 4,4'-(bis(9-ethyl-3-carbazovinylene)-1,1'-biphenyl ("BCzVBi").

20. The white organic light emitting diode ("WOLED") of claim 18, further comprising one or more undoped spacer layers.

21. The white organic light emitting diode ("WOLED") of claim 18, wherein the two deep-blue fluorescent and yellow phosphorescent emissive layers further comprise a host material.

22. The white organic light emitting diode ("WOLED") of claim 21, wherein the host material comprises 4,4'-bis(carbazol-9-yl)biphenyl ("CBP"), 4,4'-Bis(9-carbazolyl)-2,2'-Dimethyl-biphenyl ("CDBP"), N,N'-dicarbazolyl-3,5-benzene ("mCP"), 4,4',4"-tris(N-carbazolyl)triphenylamine ("TCTA"), or combinations thereof.

23. The white organic light emitting diode ("WOLED") of claim 18, further comprising one or more hole transporting layers.

24. The white organic light emitting diode ("WOLED") of claim 23, wherein the one or more hole transporting layers comprise N,N'-diphenyl-N,N-bis(1-naphthyl)-1,1'-biphenyl-4,4"-diamine ("NPB"), N,N'-dicarbazolyl-3,5-benzene ("mCP"), 1,1-bis-(4-bis(4-methyl-phenyl)-amino-phenyl)-cyclohexane ("TPAC"), or combinations thereof.

25. The white organic light emitting diode ("WOLED") of claim 18, further comprising one or more electron transporting layers.

26. The white organic light emitting diode ("WOLED") of claim 25, wherein the one or more electron transporting layers comprise 1,3,5-tris(phenyl-2-benzimidazolyl)-benzene ("TPBI"), tris(2,4,6-trimethyl-3-(pyridin-3-yl)phenyl)borane ("3TPYMB" or "TPYMB"), 1,3,5-tris(m-pyrid-3-yl-phenyl)benzene ("TmPyPB"), 1,3,5-tris(p-pyrid-3-yl-phenyl)benzene ("TpPyPB"), 4,7-diphenyl-1,10-phenanthroline ("BPhen"), or combinations thereof.

27. A white organic light emitting diode ("WOLED"), comprising:
at least one emissive layer consisting of only bis[3,5-bis(2-pyridyl)-1,2,4-triazolato]platinum(II) ("Pt(ptp)$_2$").

28. The white organic light emitting diode ("WOLED") of claim 27, further comprising at least one emissive layer comprising bis[3,5-bis(2-pyridyl)-1,2,4-triazolato]platinum(II) ("Pt(ptp)$_2$") and a host material.

29. The white organic light emitting diode ("WOLED") of claim 28, wherein the host material comprises 4,4'-bis(carbazol-9-yl)biphenyl ("CBP"), 4,4-Bis(9-carbazolyl)-2,2'-Dimethyl-biphenyl ("CDBP"), N,N'-dicarbazolyl-3,5-benzene ("mCP"), 4,4',4"-tris(N-carbazolyl)triphenylamine ("TCTA"), or combinations thereof.

30. The white organic light emitting diode ("WOLED") of claim 27, further comprising one or more hole transporting layers.

31. The white organic light emitting diode ("WOLED") of claim 30, wherein the one or more hole transporting layers comprise N,N'-diphenyl-N,N'-bis(1-naphthyl)-1,1'-biphenyl-4,4"-diamine ("NPB").

32. The white organic light emitting diode ("WOLED") of claim 27, further comprising one or more electron transporting layers.

33. The white organic light emitting diode ("WOLED") of claim 32, wherein the one or more electron transporting layers comprise 1,3,5-tris(phenyl-2-benzimidazolyl)-benzene ("TPBI").

34. The white organic light emitting diode ("WOLED") of claim 27, further comprising one or more electron and exciton blocking layers.

35. The white organic light emitting diode ("WOLED") of claim 34, wherein the one or more electron and exciton blocking layers comprise N,N'-dicarbazolyl-3,5-benzene ("mCP").

36. A method for synthesizing a white organic light emitting diode ("WOLED"), comprising:
depositing a first deep-blue fluorescent emissive layer comprising a deep-blue fluorescent dopant;
depositing a yellow phosphorescent emissive layer comprising bis[3,5-bis(2-pyridyl)-1,2,4-triazolato]platinum (II) ("Pt(ptp)$_2$"); and
depositing a second deep-blue fluorescent emissive layer comprising a deep-blue fluorescent dopant,
wherein the yellow phosphorescent emissive layer is located between the two deep-blue fluorescent emissive layers.

37. A method for synthesizing a white organic light emitting diode ("WOLED"), comprising:
depositing an emissive layer consisting of only bis[3,5-bis(2-pyridyl)-1,2,4-triazolato]platinum(II) ("Pt(ptp)$_2$").

38. The method of claim 37, further comprising the step of depositing at least one emissive layer comprising bis[3,5-bis(2-pyridyl)-1,2,4-triazolato]platinum(II) ("Pt(ptp)$_2$") and a host material.

* * * * *